United States Patent
Mikelsaar et al.

(10) Patent No.: US 10,272,122 B2
(45) Date of Patent: Apr. 30, 2019

(54) *LACTOBACILLUS PLANTARUM* **INDUCIA DSM 21379 AS ENHANCER OF CELLULAR IMMUNITY, HYPOCHOLESTEROLEMIC AND ANTI-OXIDATIVE AGENT AND ANTIMICROBIAL AGENT AGAINST *CLOSTRIDIUM DIFFICILE***

(71) Applicants: Marika Mikelsaar, Tartu (EE); Epp Songisepp, Tartu (EE); Pirje Hütt, Tartu (EE); Imbi Smidt, Tartumaa (EE); Kai Truusalu, Tartu (EE); Merle Rätsep, Tartu (EE); Siiri Koljalg, Tartu (EE); Jelena Stsepetova, Tartu (EE); Kalle Kilk, Tartu (EE); Mihkel Zilmer, Tartu (EE); Epp Sepp, Tallinn (EE); Raik-Hiio Mikelsaar, Tartu (EE)

(72) Inventors: Marika Mikelsaar, Tartu (EE); Epp Songisepp, Tartu (EE); Pirje Hütt, Tartu (EE); Imbi Smidt, Tartumaa (EE); Kai Truusalu, Tartu (EE); Merle Rätsep, Tartu (EE); Siiri Koljalg, Tartu (EE); Jelena Stsepetova, Tartu (EE); Kalle Kilk, Tartu (EE); Mihkel Zilmer, Tartu (EE); Epp Sepp, Tallinn (EE); Raik-Hiio Mikelsaar, Tartu (EE)

(73) Assignee: BIOCC OÜ, Tartu (EE)

( * ) Notice: Subject to any disclaimer, the term of this patent is extended or adjusted under 35 U.S.C. 154(b) by 0 days.

(21) Appl. No.: 15/132,286

(22) Filed: Apr. 19, 2016

(65) Prior Publication Data
US 2016/0296570 A1 Oct. 13, 2016

Related U.S. Application Data

(60) Division of application No. 14/244,284, filed on Apr. 3, 2014, now abandoned, which is a continuation-in-part of application No. 12/992,862, filed as application No. PCT/EE2009/000006 on May 12, 2009, now abandoned.

(30) Foreign Application Priority Data

May 13, 2008 (EE) .................................. 200800027

(51) Int. Cl.
| | |
|---|---|
| *A61K 35/747* | (2015.01) |
| *A23C 9/123* | (2006.01) |
| *C12R 1/25* | (2006.01) |
| *A23L 33/135* | (2016.01) |
| *A23K 10/18* | (2016.01) |
| *A23C 19/06* | (2006.01) |
| *C12N 1/20* | (2006.01) |
| *A23C 19/05* | (2006.01) |
| *A61K 35/00* | (2006.01) |
| *A61K 31/047* | (2006.01) |

(52) U.S. Cl.
CPC .......... *A61K 35/747* (2013.01); *A23C 9/1234* (2013.01); *A23C 19/061* (2013.01); *A23C 19/062* (2013.01); *A23K 10/18* (2016.05); *A23L 33/135* (2016.08); *C12N 1/20* (2013.01); *C12R 1/25* (2013.01); *A23C 19/054* (2013.01); *A23V 2002/00* (2013.01); *A23Y 2220/67* (2013.01); *A61K 31/047* (2013.01); *A61K 2035/115* (2013.01)

(58) Field of Classification Search
CPC ...................................................... A61K 35/747
See application file for complete search history.

(56) References Cited

U.S. PATENT DOCUMENTS

| | | | |
|---|---|---|---|
| 5,895,758 A | 4/1999 | Majnarich et al. | |
| 2004/0014188 A1* | 1/2004 | Whitlock ............. | A61K 8/0208 435/170 |
| 2012/0213753 A1* | 8/2012 | Cune Castellana .... | A61K 35/74 424/93.45 |

FOREIGN PATENT DOCUMENTS

| | | | | |
|---|---|---|---|---|
| WO | WO-2009138091 A2 * | 11/2009 | ........... | A23C 9/1234 |
| WO | WO-2009138092 A1 * | 11/2009 | ........... | A23C 9/1234 |

OTHER PUBLICATIONS

Platt, FM et al. Disorders of cholesterol metabolism and their unanticipated convergent mechanisms of disease. Annu. Rev. Genomics. Hum. Genet. 2014. 15: 173-194. (Year: 2014).*
Coleman, JW. Nitric oxide in immunity and inflammation. International Immunopharmacology. 2001. 1: 1397-1406. (Year: 2001).*
Kullisaar, T et al. Antioxidative probiotic fermented goats' milk decreases oxidative stress-mediated atherogenicity in human subjects. British Journal of Nutrition. 2003. 90: 449-456. (Year: 2003).*

* cited by examiner

*Primary Examiner* — Renee Claytor
*Assistant Examiner* — Susan E. Fernandez
(74) *Attorney, Agent, or Firm* — Reed Smith LLP

(57) ABSTRACT

A microorganism strain *Lactobacillus plantarum* Inducia DSM 21379 for use as hypocholesterolemic, antimicrobial and anti-oxidative agent and as enhancer of the natural defense potential of a subject. *L. plantarum* Inducia is used for reducing the level of LDL-cholesterol in blood for preventing the cholesterol metabolism disorders and cardiovascular disorders. *L. plantarum* Inducia enhances simultaneously the natural defense potential and cellular immunity, and as anti-oxidative agent enhances anti-oxidative activity of blood by reducing the level of oxidized low density lipoprotein (ox-LDL). The strain is also used as an antimicrobial agent for lowering risk of *Clostridium difficile* associated diarrhea (CDAD) by preventing germination of *C. difficile* spores and by suppressing proliferation of its vegetative cells. The compositions comprising *L. plantarum* Inducia decrease the levels of LDL-cholesterol and ox-LDL in blood, enhance the natural defense potential and lower risk of CDAD. The composition may further comprise xylitol.

1 Claim, 9 Drawing Sheets

Specification includes a Sequence Listing.

LACTOBACILLUS PLANTARUM INDUCIA DSM 21379 AS ENHANCER OF CELLULAR IMMUNITY, HYPOCHOLESTEROLEMIC AND ANTI-OXIDATIVE AGENT AND ANTIMICROBIAL AGENT AGAINST CLOSTRIDIUM DIFFICILE

CROSS REFERENCE TO RELATED APPLICATION

This application is a divisional and claims the benefit under 35 U.S.C. § 120 of U.S. application Ser. No. 14/244,284, filed Apr. 3, 2014, which is a continuation-in-part and claims the benefit under 35 U.S.C. 120 of U.S. application Ser. No. 12/992,862, filed Jul. 26, 2011, the entire contents of which are incorporated herein by reference, which is a 371 National Stage of International Application No. PCT/EE2009/000006, filed May 12, 2009, the entire contents of which are incorporated herein by reference, which claims priority from prior EE Application No. P200800027, filed May 13, 2008.

TECHNICAL FIELD

The present invention relates to the field of microbiology and nutrition referring to *Lactobacillus plantarum* Inducia DSM21379 strain which has various applications in the field of biotechnology, food industry and medicine.

BACKGROUND ART

During the past decades lactobacilli have widely been used as probiotics in functional foods. Food can be regarded as functional, if beyond adequate nutritional components it contains some natural additives (pre- or probiotics), which beneficially affect one or more target functions in the body, either improving the state of health and well-being and/or reducing disease risk. Probiotics are live microorganisms, which, when administered in adequate scientifically proven amounts, confer a health benefit on the host. Probiotic products may be conventional foods or dietary supplements. Currently a probiotic product is a strain-specific preparation targeting several host functions (anti-infectious, morphologic, immunologic, metabolic) in order to improve health by either supporting host physiologic activity or by reducing the risk of disease.

Probiotics are often used for enhancement of organisms' defence capability.

Enhancement of organisms' natural immunity has become essential in connection with the ageing of population and diseases connected with immunodeficiency (HIV infection, tissue transplantation induced immunosuppression). The cause of all of mentioned diseases is the decrease of the capability of several physiological functions of the organism (Timiras, P. S. Physiology of aging: standards for age-related functional competence In: Comprehensive Human Physiology. Greger, R (edt)/Windhorst, U (eds) Springer Verlag, 1996; pp 2391-2405).

The permeability of the intestinal mucosa frequently increases on the background of chronic inflammation. Microbial metabolites play essential role in the integrity of mucosa, e.g. short chain fatty acids (SCFA), produced by lactic acid bacteria in the colon in the case of fiber (substances of plant origin) rich diet (Roy C C, Kien C L, Bouthillier L., Levy E. Short chain fatty acids: ready for prime time?Nutr. Clin. Pract., 2006; 21:351-366).

For enhancement of mucosal barrier besides short chain fatty acids also polyamines are essential. Polyamines are linear aliphatic compound, in which amino acids are situated along the structure. Putrescine, spermidine and spermine belong to polyamines (Larqué, M., Sabater-Molina, S. Zamora E. Biological significance of dietary polyamines. Nutrition 2007; 23(1): 87-95). Polyamines are produced by decarboxylation from amino acids ornithine and arginine. Putrescine is produced straight from ornithine; arginine, is primarily converted into agmantine which is then converted into putrescine (Halaris A, Plietz, Agmatine: metabolic pathway and spectrum of activity in brain. CNS Drugs, 2007; 21: 885-90).

The physiological impact of polyamines is targeted to cell growth and differentiation, regulation of immune cells and inflammatory response, and several other effects. Polyamines possess the ability to induce apoptosis, avoiding the hyperproliferation of epithelium and destruction of primary cancer cells (Moinard C, Cynober L, De Bandt J P Polyamines: metabolism and implications in human disease. Clin Nutr. 2005; 24: 184-197). Polyamines are produced endogenously or they are obtained actively from food.

In the case of the damage of epithelial cells, the production of polyamines by the intestinal microflora is considered one of the compensatory mechanisms for modification of immune response and apoptosis regulation. Lactobacilli comprise majority of microflora of the proximal colon. Lactobacilli produce polyamines through decarboxylation of amino acids, particularly at the high pH of the intestinal content (Lonvaud-Funel A, Biogenic amines in wine: role of lactic acid bacteria. FEMS Microbiol. Letters, 2001: 199: 9-13). On the other hand, strains of *Lactobacillus acidophilus* utilize putrescine and reduce odour of faces (WO 2008/019887, BASF AG).

Probi AB Estonian patent EE03597 discloses pharmaceutical composition that contains *L. plantarum* strains 299 and 299v together with arginine for prevention translocation of intestinal microbes during liver injury. Also in this patent no information is available concerning the end products of arginine utilization (putrescine, cadaverine, tyramine, enhancement of NO or antioxidativity) by *L. plantarum*, which are responsible for aforementioned effect. In close relationship with previous patent another Probi AB patent EE04097 does not disclose the polyamines or NO production ability of mentioned *L. plantarum* strains.

It has been demonstrated, that *Lactobacillus rhamnosus* GG could enhance NO production in the epithelial cells of the intestine or by proinflammatory cytokines and it has been indicated, that beneficial effects of *Lactobacillus rhamnosus* GG could be due to the production of NO by macrophages and epithelial cells (Korhonen K, Reijonen T M, Remes K, Malmstrom K, Klaukka T, Korppi M. Reasons for and costs of hospitalization for paediatric asthma: A prospective 1-year follow-up in a population-based setting. Pediatr Allergy Immunol 2001: 12:331-338). It has been demonstrated, that NO protects mucosa for damages and excessive permeability, arising after reperfusion (Payne D, Kubes P. Nitric oxide donors reduce the rise in reperfusion-induced intestinal mucosal permeability. Am J Physiol. 1993: 265 (1 Pt 1):G189-G195).

USA patent application US20060078595 (Friesland Brands B.V.) discloses method to avoid the excessive permeability of the intestinal barrier in newborns by glutamate and its precursors as well as by polyamines spermidine, spermine, putrescine in the case of different syndromes (malnutrition, allergy, sepsis, translocation of microbes, endotoxemia, viral diarrhoea). *Lacobacillus Reuteri* (BIO-GAIA) served as glutamate source.

Polyamine spermidine has inflammation-lowering property. It has been demonstrated that spermidine, when added to human monocytes stimulated with lipopolysaccharides, inhibits effectively the synthesis of TNF, IL-1, IL-6 and other proinflammatory cytokines (Zang M, Caragine T. Wong H et al. Spermine inhibits proinflammatory cytokine synthesis in human mononuclear cells: a counter regulatory mechanism, that restrains the immune response. J. Exp. Med., 1997, 185: 1759-1768). Matsumoto with co-authors described the suppression of proinflammatory cytokine synthesis (Matsumoto M, Ohisshi H, Benno Y Impact of LKM512 yoghurt on improvement of intestinal environment of the elderly. FEMS immunol. Medical Microbiol, 2001; 31:181-186). *Bifidobacterium lactis* LKM512 comprising yoghurt administration to elderly decreased the glukoprotein haptoglobuline caused inflammatory acute phase response due to IL-1, Il-6 and TNF-alfa, but the probiotic administration was also accompanied by decrease of mutagenicity of the intestinal epithelial cells. At the same time it is evident, that different lactic acid bacteria incl. lactobacilli species and strains differ by their ability to induce pro- and anti-inflammatory cytokines and non-specific cellular immune response. Up to now, no *lactobacillus* species/strain has been described, which would be able to produce physiologically relevant amounts of polyamines, which could be detected in urine after the consumption of this particular strain comprising composition and which promote simultaneously the adaptive activation of immunocytes due to interleukin IL-6.

Proinflammatory cytokine IL-6 synthesis has been described after 24 h of stimulation with different strains of *Bifidobacterium animalis* and *Lactobacillus rhamnosus* (Miettinen M., Vuopio-Varkila J, Varkila K. Synthesis of human tumour necrosis factor alpha, interleukin-6 and interleukin-10 is induced by lactic acid bacteria. Infection and Immunity, 1996, 64:5403-5408). It is important to observe inflammation markers like counts of leucocytes (WBC) and amount of CRP in sera on the induction of IL-6 (Kiecolt-Glaser J K, Preacher K J, MacCallum R C et al. Chronic stress and age-related increases in the proinflammatory cytokine IL-6, PNAS, 2003; 100:9090-9095) to avoid the overproduction of IL-6. Aforementioned is associated with cardiovascular diseases, arthritis, type II diabetes, cancer, periodontal diseases, cachexy and decrease of organisms functions (Rose-John S., J. Scheller, G. Elson, and S. A. Jones. Interleukin-6 biology is coordinated by membrane-bound and soluble receptors: role in inflammation and cancer J. Leukoc. Biol., Aug. 1, 2006; 80 (2): 227-236).

*Lactobacillus plantarum* is a widely spread representative of the genus *Lactobacillus*. Aforementioned *lactobacillus* species is present on fermented plants (sauerkraut, pickles, and silage), fermented dairy/meat products (cheese, salami) as well as in human gastrointestinal tract. *Lactobacillus plantarum* is able to reorganize its metabolism according to environmental conditions.

Probiotic *Lactobacillus plantarum* is available in probiotic foods as well as in food supplements (e.g. *Lactobacillus plantarum* 299v DSM 9843, Probi AB, Sweden, Skånemejeriers' ProViva probiotic brand in Sweden or as one of the components in bacterial composition VSL#3 (VSL Pharmaceuticals, Inc. USA). WO2007/108764 (Probac AB) discloses the action mechanisms of *Lactobacillus plantarum* strains, which are able to enhance immunotolerance in the case on autoimmune coeliac disease.

Cheese as a probiotic carrier has several controversial aspects. Incorporation lactobacilli of human origin into a food product different from other milk-based products and having a long ripening period could be complicated. At the same time fat and protein-rich cheese matrix protects a probiotic microbial strain throughout the passage of gastrointestinal tract better than other milk products (yoghurt, kefir). Antimicrobial and antioxidative probiotic cheese has been produced by using *Lactobacillus fermentum* ME-3 (DSM 14241) (Estonian patent EE04580, Russian patent RU2284354, U.S. Pat. No. 6,190,879). European patent EP1064857B1 (Snow Brand Milk Products Co Ltd., 2004) discloses methods for production substances incl. putrescine with lactobacilli, bifidobacteria and propionibacteria from Gouda cheese milk ultrafiltration. These methods are either polymerization reactions for incorporating putrescine into casein or vice versa—purification of these compounds by ultrafiltration, that have already been produced into milk, methods are different from this one described in present invention, where putrescine, that has been produced by lactobacilli into milk is still present in cheese after 30 days of ripening. Various non-starter lactobacilli have been described (*Lactobacillus paracasei, Lactobacillus curvatus*), which are able to gain energy for proliferation from ornithine (ornithine is released from milk casein arginine) after depletion of carbohydrates (Laht T.-M., Kask S., Elias P., Adamberg K., Paalme T. Role of arginine in the development of secondary microflora in Swiss-type cheese. Int. Dairy Journal, 2002, 12: 831-840).

Till now no *lactobacillus* species/strain have been described, the culture of which produces NO and additionally physiologically relevant amounts of polyamines in food product, whereas the latter could be detectable in urine after the consumption of this strain comprising food product (cheese) or composition and that is able to regulate through polyamines the apoptosis of intestinal epithelium and increase the count of the mucosal lymphfollicles and blood monocytes, regulating the condition of mucosa by NO and antioxidative compounds and to enhance the activation of immune cells particularly the activation of macrophages by central interleukine.

One of the factors leading to cardiovascular disease (CVD) is abnormally elevated cholesterol level. Recently, the view of high cholesterol as damaging agent has been reverted to abnormality of its particles, particularly low density lipoprotein-cholesterol (LDL-c). LDL-c accounts 60-70% of total cholesterol. LDL-c particles carry cholesterol, triglycerides, fat-soluble vitamins and antioxidants. The LDL-cholesterol is an important modulator for prevention of atherosclerosis and maintenance of cardiovascular health. Thus, the LDL-c is widely recognized as an established cardiovascular risk marker. The close relation between mucosal epithelial cells of host gut and microbiota is of utmost importance for health. Among indigenous microbiota of gastrointestinal tract (GIT) the lactic acid bacteria assimilate cholesterol from dietary products (Gilliland, S. E., Nelson, C. R., Maxwell, C., Assimilation of cholesterol by *Lactobacillus acidophilus*. Appl Environ Microbiol 1985; 49, 377-381). In patent of Cuñé Castellana, 2009 (EP2485743131; AB Probiotics S.A.) *Lactobacillus plantarum* strains CECT 7528, CECT 7526 and CECT 7529 as single or in composition demonstrated both in vitro and in vivo the cholesterol lowering ability. These strains have bile salt hydrolases (BHS) activity, also the antagonistic activity to inhibit the growth of pathogenic strains (*Salmonella enterica* Enteritidis, *Salmonella enterica* Typhimurium, *Yersinia pseudotuberculosis, Clostridium perfringens, Clostridium ramnosus, Enterococcus faecalis*) and can be used as probiotic bacteria.

Pereira et al. (Pereira, I). I., McCartney, A. L., Gibson, G. R., An in vitro study of the probiotic potential of a bile-salt-hydrolyzing *Lactobacillus fermentum* strain, and determination of its cholesterol-lowering properties. Appl Environ Microbiol. 2003; 69, 4743-4752) have demonstrated the role of short-chain fatty acid concentrations, specifically the molar proportion of propionate and/or bile salt deconjugation as the major mechanism involved in the purported cholesterol-lowering properties of *L. fermentum*.

However, the effect of *Lactobacillus* spp strains on levels of serum cholesterol (and cholesterol fractions) is strain-specific and dependant on the origin and properties of a certain strain (Tanaka, H., K. Doesburg, T. Iwasaki and I. Mireau, Screening of lactic acid bacteria for bile salt hydrolase activity. J. Dairy Sci. 1999; 82: 2530-2535).

Disturbed Microbial Ecology of Gut

The colonic microbiota is well stabilised and due to mucosal microbiota it does not change easily. But it is well known that the application of broad-spectrum antimicrobial preparations for treatment of infections and inflammatory complications may cause profound imbalance among GI microbiota.

*Clostridium difficile* Infection

*Clostridium difficile* was identified in the 1970's as the causative agent of antibiotic associated diarrhoeae. The anaerobic spore-forming intestinal pathogen *Clostridium difficile* is spread in hospitals and elderly homes (Britton, R. A., Young, V. B. Interaction between the intestinal microbiota and host in *Clostridium difficile* colonization resistance. Trends Microbiol. 2012; 20, 313-319). *C. difficile* infection is initiated by infection with *C. difficile* spores. Endospore production is vital for the spread of *Clostridium difficile* infection. In order to cause disease, these spores must germinate and return to vegetative cell growth (Burns D. A, Heap J. T. Minton N. P. *Clostridium difficile* spore germination: an update. Res Microbiol. 2010; 161(9):730-4). *C. difficile* elicits disease through the actions of secreted toxins, which are produced by vegetative cells, not by spores.

In a quarter of patients (25%) infected with *C. difficile* develop serious sequela such as pseudomembraneous colitis (PMC). *C. difficile*-associated diarrhea (CDAD) increases mortality rates, lengthens hospitalization and dramatically increases overall health care costs. *Clostridium difficile* infection recurs in about 20% of patients, and increases to 40% and 60% with subsequent recurrences (Kelly, C. P., LaMont, J. T. *Clostridium difficile*—more difficult than ever. N Engl J Med. 2008; 359, 1932-1940). Antimicrobial treatment disrupts the complex balance of diverse microorganisms and is a key factor in the pathogenesis of *C. difficile* colonization and disease. Preservation and restoration of the microbial diversity could represent novel strategies. The crucial moment in prevention and treatment of this disease is to find the possibility to reconstitute the alteration of intestinal microbiota during and after antibiotic therapy with various regimens incl. administration of probiotics. Most probiotics colonize the gut temporarily, produce bactericidal acids and peptides and promote "competition" among microbes by competing for nutrients and epithelial adhesion. These effects appear to reduce the favourability of the environment for *C. difficile*. Previous studies suggest that probiotics for prevention of CDI include combination *L. acidophilus* and *L. casei, S. boulardii*, or *L. rhamnosus*. In addition, a dosage of >$10^9$ cfu/day is more effective than lower doses.

The antimicrobial activity of probiotic strains is one of the suggested mechanisms for competition with *C. difficile*. Lactic acid bacteria produce short chain fatty acids that lower the pH of the local gut environment as well as prevent the adhesion of *C. difficile* (McFarland, L. V., Beneda, H. W., Clarridge, J. E., Raugi, G. J. Implications of the changing face of *C. difficile* disease for health care practitioners. Am J Infect Control. 2007; 35, 237-253). Next, the possibility for intestinal barrier protection with probiotics may result in interfering with the binding of *C. difficile* toxins A and B to colonic epithelial cells thus stabilizing gut permeability and inhibiting development of pseudomembranes on epithelia of gut.

Strain-specificity of lactobacilli is an important factor to take into consideration when looking for potential probiotics in the prevention of *C. difficile* infection or binding the *C. difficile* toxins (Tejero-Sariñena S., Barlow J., Costabile A, Gibson G. R., I. Rowland Antipathogenic activity of probiotics against *Salmonella Typhimurium* and *Clostridium difficile* in anaerobic batch culture systems: Is it due to synergies in probiotic mixtures or the specificity of single strains?Anaerobe 2013: 24; 60-65).

Furthermore, some clinical trials could not reach statistical evidence to demonstrate the effect for the prevention of *Clostridium difficile* associated diarrhea (CDAD) of certain probiotics. The authors of a large, randomized trial including 2941 elderly adults with antibiotic exposure noted that those who received probiotics (a multistrain preparation of *Lactobacillus acidophilus* and *Bifidobacterium bifidum*) did not show a risk reduction for CDI (RR 0.71; 95% CI 0.34-1.47; p=0.35) (Allen, S. J., Wareham, K., Wang, D., Bradley, C., Hutchings, H., Harris, W., Dhar, A., Brown, H., Foden, A., Gravenor, M. B., Mack, D. Lactobacilli and bifidobacteria in the prevention of antibiotic-associated diarrhoea and *Clostridium difficile* diarrhoea in older inpatients (PLACIDE): a randomised, double-blind, placebo-controlled, multicentre trial. Lancet, 2013: 382, 1249-1257). After years of trials with different probiotics for treatment of CDI the strain, dose, and duration of probiotics are still under discussion (Naaber, P., Mikelsaar, M., Interactions between Lactobacilli and antibiotic-associated diarrhea. Adv Appl Microbiol, 2004: 54, 231-260).

Xylitol Application

Xylitol is a 5-C sugar alcohol, e.g. pentitol, and is found in plants, fungi and algae. Xylitol is an important intermediate product in mammalian carbohydrate metabolism; i.e. human blood contains up to $8 \times 10^{-5}$ M of xylitol. Consumed xylitol is not absorbed completely and the unabsorbed part can be used as a dietary fibre for bacterial fermentation to convert xylitol to short fatty acid chains utilized in energy pathways. Xylitol influences the growth of some species of gut microbiota in the large intestines stimulating the growth and activities of indigenous microbiota. One gram of xylitol contains 2.4 kcal as compared to one gram of glucose which has 3.87 kcal. Xylitol is advertised as "safe" for diabetics and individuals with hyperglycaemia (Talbot J. M., K. P. Fisher The Need for Special Foods and Sugar Substitutes by Individuals with Diabetes Mellitus. Diabetes Care 1978: 1; 231-240).

In our previous studies on Caco-2 cell lines we have discovered that 1% xylitol prevented the adhesion of vegetative cells of *C. difficile* reference strain VPI 10463, seemingly blocking the receptors on cells. In an applied hamster model (Naaber, P., Lehto, E., Salminen, S., Mikelsaar, M. Inhibition of adhesion of *Clostridium difficile* to Caco-2 cells. FEMS Immunol Med Microbiol. 1996: 14, 205-209) 1 ml of 20% xylitol solution together with *Lactobacillus rhamnosus* GG significantly protected animals from development of severe enterocolitis (Naaber, P., Lehto, E., Salminen, S., Mikelsaar, M., 1996. Inhibition of adhesion of *Clostridium difficile* to Caco-2 cells. FEMS Immunol Med Microbiol, 14, 205-209). In these experimental studies with xylitol in combination with probiotic *L. rhamnosus* GG the vegetative cells of *Clostridium difficile*, precultivated in laboratory anaerobic environment, have applied for inoculation of cell cultures or hamsters.

In opposite, in clinical practice or elderly home the infection develops from inoculation with *C. difficile* extremely resistant spores surviving in the aerobic environment of these facilities. The spores start to germinate inside the intestine of host.

Some authors have postulated that in the animal model some of sugars similarly to glucose could block the expression of toxins A and B of *C. difficile* (Karlsson, S., Burman, L. G., Akerlund, T. Induction of toxins in *Clostridium difficile* is associated with dramatic changes of its metabolism. Microbiology, 2008: 154, 3430-3436).

There is still a need for probiotic strains effective in enhancing of cellular immunity, decreasing LDL-cholesterol as well as in lowering the risk of *Clostridium difficile* infection.

Disclosure of the Invention

The purpose of the present invention is to provide a strain *Lactobacillus plantarum* Inducia DSM 21379 for use as hypocholesterolemic agent for decreasing the level of LDL-cholesterol in blood for preventing the cholesterol metabolism disorders and consecutive cardiovascular disorders.

Another purpose of the instant invention is to provide the aforesaid strain for use as an antimicrobial agent for lowering risk of *Clostridium difficile* associated diarrhoeae (CDAD) by preventing germination of *Clostridium difficile* spores and by suppressing proliferation of *Clostridium difficile* vegetative cells.

The next purpose of this invention is to provide *Lactobacillus plantarum* Inducia DSM 21379 for use as anti-oxidative agent for enhancing anti-oxidative activity of blood by reducing the level of oxidized low density lipoprotein (ox-LDL) and by enhancing the total anti-oxidative activity (TAA) of a composition comprising said strain.

The current invention also relates to the compositions comprising *L. plantarum* Inducia DSM 21379 for decreasing the levels of LDL-cholesterol and ox-LDL in blood, lowering risk of CDAD and for enhancing the natural defense potential and cellular immunity of a human.

Due to the fact that *L. plantarum* Inducia DSM 21379 produces polyamines from ornithine and glutamate, nitric mono-oxide (NO), the composition comprising said strain possesses antioxidative activity and improves the intestinal barrier function, increases the number of immunocytes in blood and induces cytokine synthesis for enhancement of organisms' natural defense. *Lactobacillus plantarum* Inducia DSM 21379 is used as enhancer of the natural defense potential and cellular immunity of a subject, and simultaneously as anti-oxidative agent as well as hypocholesterolemic agent.

The composition may further comprise xylitol. The composition can be used for the production of food products, food supplements or pharmaceutical or veterinary products. The food product can be dairy product (fermented milk, cheese) or meat product, sweets, etc. The food supplement may be may be used in powder (capsules, lozenges, tablets, powder sachets etc.) or liquid (ampoules) form. The strain may be used in compositions in freeze-dried form.

The fact that the microbial strain originates from the intestinal tract of a healthy child proves its GRAS (generally recognized as safe) status i.e. that this strain of microorganism is harmless for human organism and is suitable for oral application compositions.

Antimicrobial Activity

*Lactobacillus plantarum* Inducia DSM 21379 expresses in vitro on MRS agar medium antagonistic activity against several enteric pathogens (Table 1).

Functional Properties

TABLE 1

*Lactobacillus plantarum* Inducia DSM 21379 antimicrobial activity against pathogens and non-starter lactobacilli on modified MRS agar medium (pathogen growth inhibition zone, mm)

| Pathogen | Growth inhibition zone (mm) |
| --- | --- |
| Non-starter lactobacilli (NSLAB) | 2.67 ± 3.4 |
| *Listeria monocytogenes* | 22.7 ± 2.4 |
| *Yersinia enterocolitica* | 11.2 ± 2.7 |
| *Salmonella enteritidis* | 22.1 ± 1.9 |
| *S. typhimurium* | 20.8 ± 2.8 |
| *Shigella sonnei* | 24.0 ± 0.1 |
| *Escherichia coli* | 23.0 ± 1.4 |
| *Enterobacter sakazakii* | 18.1 ± 1.8 |
| *Campylobacter jejuni* | 12.0 ± 7.6 |

*Lactobacillus plantarum* Inducia DSM 21379 antimicrobial activity in vitro in streak-line procedure (antimicrobial effect of metabolites) was highest against *E. coli*, followed by growth inhibition of *Salmonella* sp., *Shigella* and *Listeria*. The lowest antimicrobial activity was detected against other lactobacilli (NSLAB).

Total Antioxidative Activity of *Lactobacillus plantarum* Inducia DSM 21379

Method. For the detection of TAA and TAS of the microbial cells, the strain *L. plantarum* Inducia was incubated in MRS broth (Oxoid, U.K.) for 24 h at 37° C. Microbial cells were harvested by centrifugation (1500 RPM, during 10 min) at 4° C. and the pellet was washed with isotonic saline (4° C.) and suspended in 1.15% KCl (Sigma, USA). The density of the suspension was $OD_{600}$ of $1.1 \times 10^9$ bacterial cells $ml^{-1}$). Total antioxidative activity (TAA) was assessed by using the linolenic acid test (LA-test). (Kullisaar, T, Songisepp, Mikelsaar M, Zilmer, K, Vihalemm, T, Zilmer, M. British J of Nutrition. Antioxidant probiotic fermented milk decreases oxidative stress-mediated atherogenicity in human. 2003: 90, 2, 449-456) and total antioxidative status (TAS) was measured by commercial kit (TAS, Randox Laboratories Ltd., UK).

TABLE 2

Total antioxidative activity (TAA) and total antioxidative status (TAS) of *Lactobacillus plantarum* Inducia DSM 21379

| Strain | TAA (%) | TAS (mmol/l) |
| --- | --- | --- |
| *L. plantarum* Inducia DSM 21379 | 26 ± 1.2 | 0.13 ± 0.04 |
| *L. plantarum* DSM 21380 | 22 ± 5 | 0.05 ± 0.02 |

Production of Nitrogen Mono-Oxide (NO)

Method. Nitrogen mono-oxide production measurements were carried out with 24 h old intact cells in 500μ of MRS broth with Apollo 4000 free radical analyzer (WPI, Berlin, Germany) and electrodes of type. ISO-NOP electrode signals were registered during 5-7 minutes. Mean signal strength was calculated. Each experimental point was measured in 4 independent parallels and each parallel was measured twice. NO concentration was calculated according to the standard curves correlation with the strength of the electrodes signal.

TABLE 3

NO concentration (μM) produced by *Lactobacillus plantarum* DSM 21379

| Strain number | NO concentrations (μM) |
|---|---|
| L. plantarum DSM 21379 | 2.7 ± 1.2 |
| L. plantarum DSM 21380 | 2.6 ± 0.8 |
| L. coprophilus | 2.1 ± 1.1 |
| L. plantarum | 2.1 ± 0.9 |
| L. paracasei ssp paracasei strain no 1 | 1.3 ± 0.8 |
| L. paracasei ssp paracasei strain no 2 | 1.8 ± 0.9 |
| L. paracasei ssp paracasei strain no 3 | 2.8 ± 1.6 |
| L. buchneri | 2.0 ± 1.1 |

In Vitro Polyamines Production of *Lactobacillus plantarum* Inducia DSM 21379

Method. Microbial strains were suspended in physiological saline according to McFarlandi turbidity standard ($10^9$ CFU/ml) and 0.5 ml of each strain suspension was seeded into decarboxylation medium (á 4.5 ml) and incubated at 37° C. for 4 days (Bover-Cid and Holzapfel W. H. Improved screening procedure for biogenic amine production by lactic acid bacteria. Int J food Microbiol 1999; 53, (1); 33-41(9)).

For detection of BA 200 μl of medium was derivatized for GC analyze by modified method of Nakovich (Nakovich, L. Analysis of biogenic amines by GC/FID and GC/MS. Thesis, Va. polytechnic institute, USA. 2003).

GC analysis were carried out by gas chromatograph HP 6890 Series GC System, with capillary colonna HP-5 19091J-413 (30 m×0.32 mm; 0.25 μm) with 160° C. 1 min, 20° C./min 280° C. 15 min; and detector (FID) 300° C. both in control strain as well as in *Lactobacillus plantarum* Inducia DSM 21379. No histamine production was detected (Table 4).

Subjects no 3, 6, 9, 11, 14, 15, 19, 20, 22, 23, 24 and 25. Four samples: at the recruitment (1), after consumption of probiotic cheese (2), after wash-out period (3) and after consumption of control cheese (4).

Figure 3:
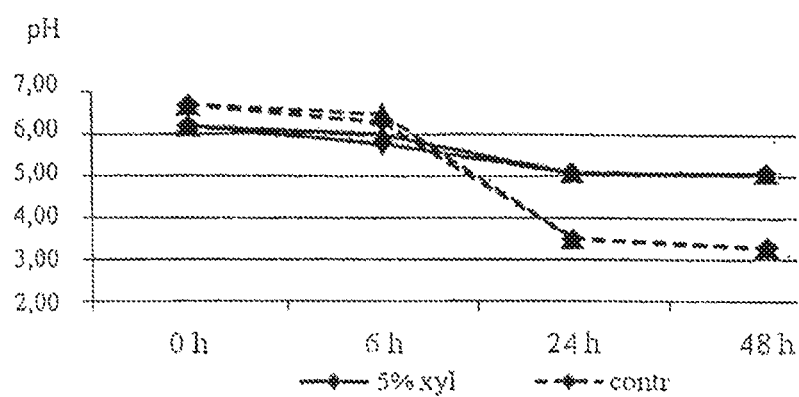

FIG. 3. The pH values of in *L. plantarum* Inducia DSM 21379 in xylitol containing and control modified MRS media in microaerobic and anaerobic environment.

Figure 4:
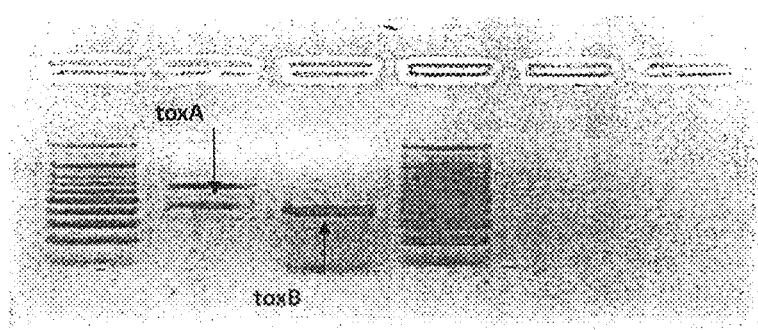

FIG. 4. Presence of toxA and B genes in *C. difficile* VPI 10643 by reverse transcription (RT) and real-time PCR amplification (qPCR).

Figure 5:
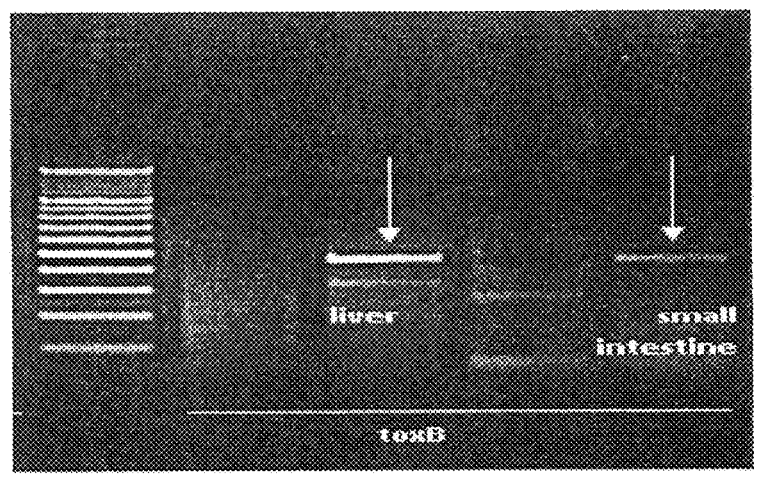

FIG. 5. Presence of toxB gene in liver and small intestine of a hamster treated with ampicillin and *C. difficile* by reverse transcription (RT) and real-time PCR amplification (qPCR).

Figure 6:
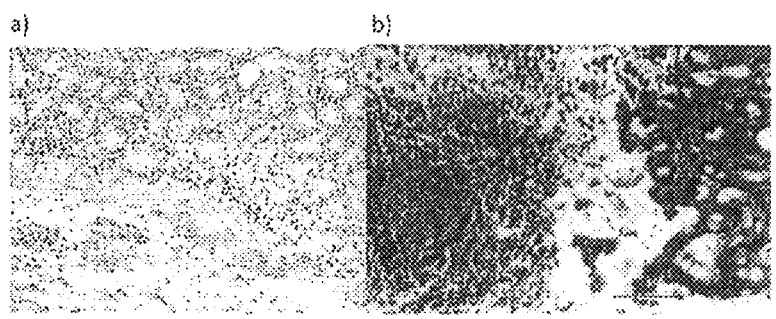

FIG. 6. a) Normal mucosa of large intestine after probiotic administration and b) mucosa with *C. difficile* infection.

Figure 7:
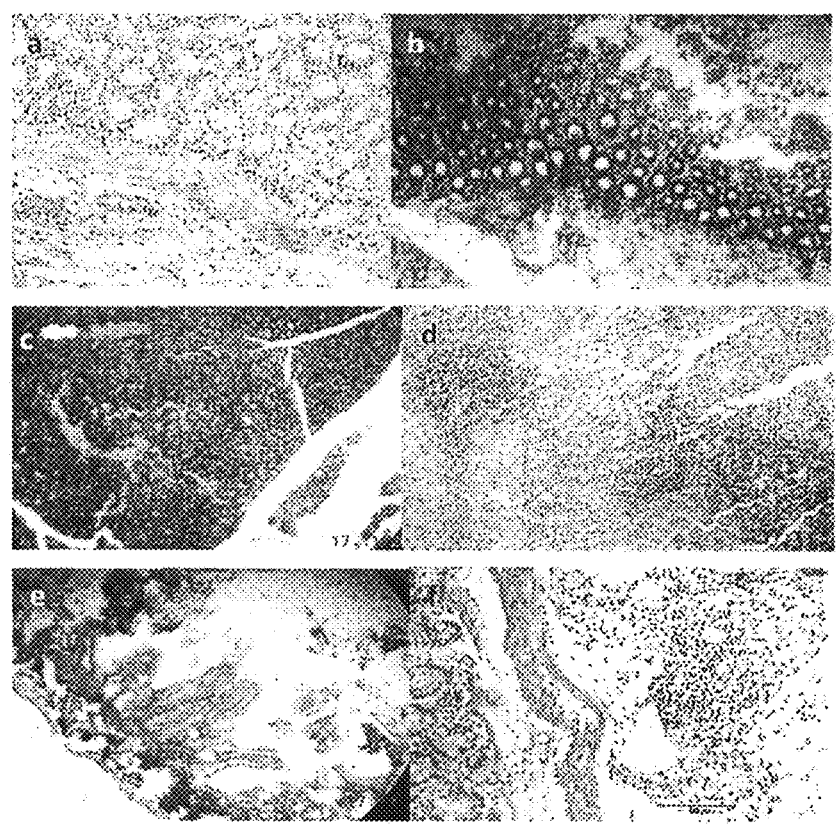

FIG. 7. Morphological changes in experimental CDAD infection. Moderate hyperaemia in a) small intestine and b) large intestine and intense hyperaemia in c) pancreas and d) spleen. Pseudomembrane in e) small intestine and PMN infiltration with pseudomembrane f) in large intestine.

DESCRIPTION OF THE EMBODIMENTS

Example 1. Obtaining Needed (Optimal) Viable Counts of *Lactobacillus plantarum* Inducia DSM 21379 in Food Product Test with Estonia Cheese Method. Microorganism *Lactobacillus plantarum* Inducia DSM 21379 was added to the cheese milk of Dairy Cooperative E-Piim, (inoculation dose $3 \times 10^8$ CFU/vat) and the milk was renneted (25 min). The curds were cut (25 min), heated (34° C. 15 min), dried (25 min), pressed, drained (1 h), salted in brine (12° C.; 20% NaCl; pH 4.7) 20 h, drained and dried (8 h), backed into plastic and ripened at 12° C. for at least 4 weeks.

TABLE 4

Production of polyamines in vitro in the decarboxylation medium (Arena, M. E. and Manca de Nadra, M. C. Biogenic amine production by *Lactobacillus*. J Appl Microbiol, 2001; 90; 158-162)

| | Polyamines (μg/ml) and biogenic amines | | | | | | | | |
|---|---|---|---|---|---|---|---|---|---|
| | Arginine | | Glutamine | | Lysine | | Ornithine | | Histi-dine |
| Sample | Putrescine | Cadaverine | Putrescine | Cadaverine | Putrescine | Cadaverine | Putrescine | Cadaverine | Cadaverine |
| L. plantarum Inducia DSM 21379 | 0 | 0.4 | 1.2 | 0.5 | 0 | 0.4 | 1.9 | 0 | 0 |
| L. plantarum DSM 2137980 | 0 | 0 | 0 | 0 | 0 | 0.3 | 0.5 | 0.6 | 0 |

Figure 1:
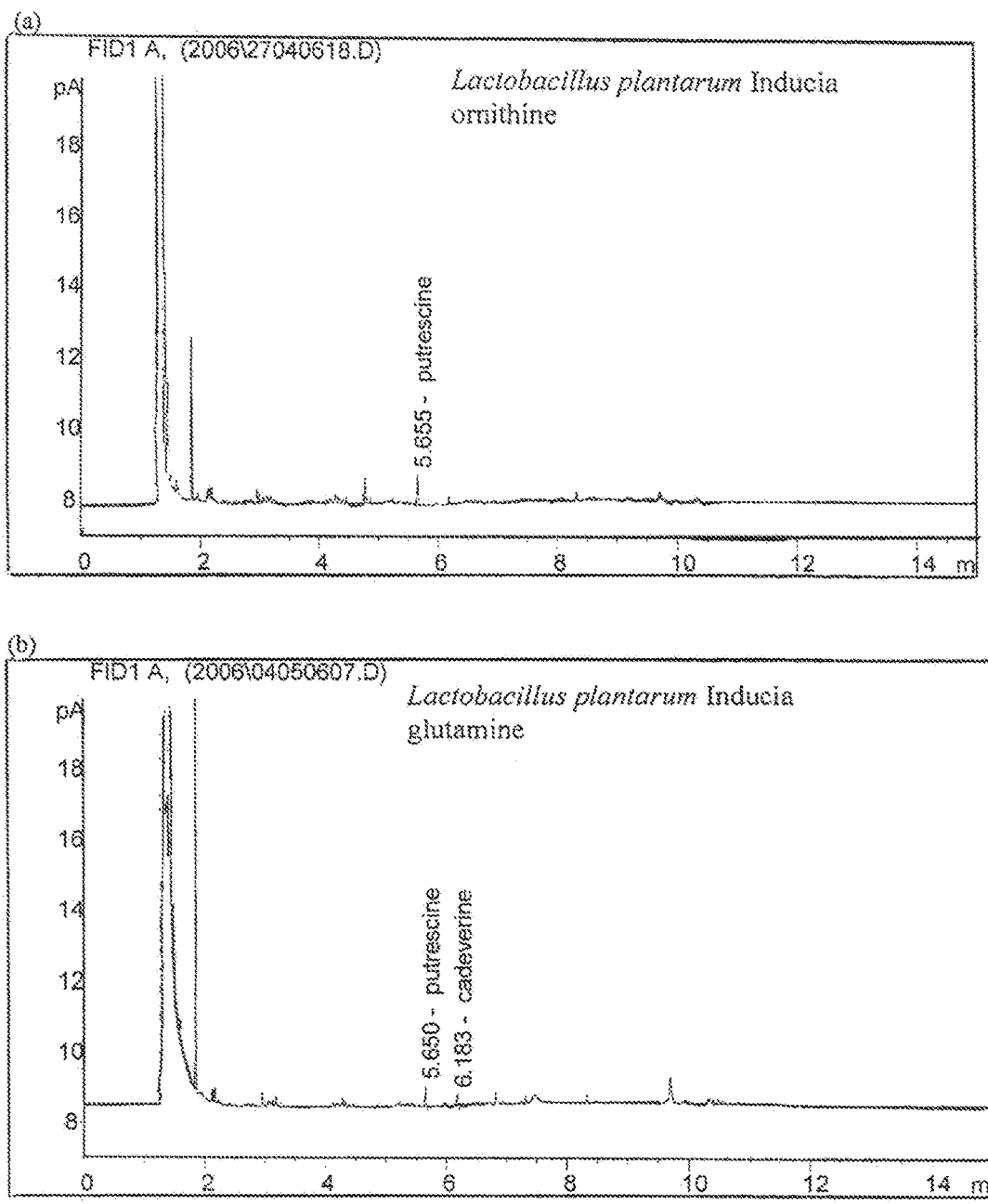
FIG. 1. Production of polyamines by *L. plantarum* DSM 21379 in vitro in the decarboxylation medium (Arena, M. E. and Manca de Nadra, M. C. Biogenic amine production by *Lactobacillus*. J Appl Microbiol, 2001; 90; 158-162) (a) from ornithine (b) from glutamine.

*Lactobacillus plantarum* strain Inducia DSM 21379 is able to produce cadaverine from arginine, putrescine both from glutamine as well as from ornithine. But the control strain was able to produce putrescine in low amounts only from ornithine (FIG. 1). Traces of cadaverine were detected

TABLE 5

Dynamics of microflora in *Lactobacillus plantarum* Inducia DSM 21379 comprising cheese.

| Sample | *L. plantarum* Inducia DSM 21379 comprising cheese | | | Control cheese | | |
|---|---|---|---|---|---|---|
|  | Day 14 | Day 21 | Day 30 | Day 14 | Day 21 | Day 30 |
| total counts | $8 \times 10^8$ | $4 \times 10^8$ | $10^{10}$ | $2 \times 10^8$ | $3 \times 10^8$ | $2 \times 10^8$ |
| *Lactobacillus* sp | $5 \times 10^8$ | $2 \times 10^8$ | $10^{10}$ | $10^5$ | — | $3 \times 10^3$ |
| *L. plantarum* | $5 \times 10^8$ | $2 \times 10^8$ | $10^{10}$ | — | — | $3 \times 10^3$ |
| cocci | $3 \times 10^8$ | $2 \times 10^8$ | $10^9$ | $2 \times 10^8$ | $3 \times 10^8$ | $10^8$ |
| spore-forming microbes | — | — | $10^3$ | — | $10^7$ | $10^8$ |
| *L. casei* | — | — | — | $10^5$ | — | — |

I. *Lactobacillus plantarum* Inducia DSM 21379 for Enhancing Cellular Immunity

Example 2. Production of Polyamines in Food Product by *Lactobacillus plantarum* Inducia DSM 21379

Method. Cheese samples were extracted (20 ml 50% methanol solution was added to 10 g of cheese and incubated at 45° C. for 1 h, cooled to 30° C. and centrifuged) and 200 µl of upper layer was derivatized for GC analyze by modified method of Nakovich (Nakovich, L. 2003 Analysis of biogenic amines by GC/FID and GC/MS).

GC analysis were carried out by gas chromatograph HP 6890 Series GC System, with capillary colonna HP-5 19091J-413 (30 m×0.32 mm; 0.25 µm). The column temperature program 160° C. 1 min, 20° C./min 280° C. 15 min; and detector (FID) 350° C.

The production of putrescine and tyramine was related to that: in different lots in comparison with control-cheese putrescine content increased 3-11 times and tyramine content accordingly 2-5 times.

*Lactobacillus plantarum* Inducia DSM 21379 belongs to the facultatively heterofermentative group of lactobacilli and therefore the content of tyramine in cheeses was significantly lower than that of strains of OHEL group. On the other hand, the content of putrescine was higher.

TABLE 6

Biogenic amines and polyamines in *Lactobacillus plantarum* Inducia DSM 21379 comprising test-cheeses from industrial test-trials

| Sample | Viable counts of strain incorporated into cheese (CFU/g) at day 3-4 after | Amines (mg/kg) | | | Viable count of *L. Plantarum* Tensia DSM 21379 in |
|---|---|---|---|---|---|
|  |  | Tyra-mine | Putres-cine | Cadav-erine |  |
| *L. plantarum* Inducia DSM 21379, 1. Batch | $3 \times 10^8$ | 4.83 | 20.28 | 0 | $2 \times 10^7$ |
| Control cheese 1. Batch | — | 2.31 | 1.82 | 0 | — |
| *L. plantarum* Inducia DSM 21379, 2. Batch | $3.3 \times 10^7$ | 13.57 | 24.67 | 0 | $2 \times 10^6$ |
| Control cheese 2. Batch | — | 2.63 | 6.64 | 0 | — |

Permitted concentration of tyramine in food e.g. in cheese is 200 mg/kg (Karovicova and Kohajdova. Biogenic amines in food. Chem pap. 2005; 59 (1); 70-79; Larqué, M., Sabater-Molina, S. Zamora E. Biological significance of dietary polyamines. Nutrition 2007; 23(1): 87-95). Tyramine is considered toxic in concentrations of 1000-8000 mg/kg.

Putrescine is considered toxic if detected in organism in concentration of 2000 mg/kg per body weight and total toxicity of polyamines is >300 mg/kg per food product (Larqud, M., Sabater-Molina, S. Zamora E. Biological significance of dietary polyamines. Nutrition 2007; 23(1): 87-95).

By consumption of 100 g *Lactobacillus plantarum* Inducia DSM 21379 comprising cheese the subject gets ca 3 mg of putrescine. Thus, in the case of person of 70 kg the concentration is up to 50 µg per kg, which does not express toxic effect.

Example 3. Enhancement of Defence Capability of Intestinal Mucosa with *Lactobacillus plantarum* Inducia DSM 21379 Comprising Food In the experimental model with NIH mice 3 groups of mice consumed different cheeses during 30 days (control cheese with no additives, *Lactobacillus plantarum* strain Inducia DSM 21379 $2 \times 10^8$ cfu/g comprising cheese).

Cheese was administered to mice at night (normal awake time for mice) 4.4 g/per mouse, daily ad libitum regular commercial diet. Consumed amount of cheese was 3.5-4.2 g/per night.

Mice stayed in good condition, no changes in fur and digestion was detected. Cheese administration caused increase of body weight: body weight at the beginning of the trial was 22.9-29.8 g and at the end of the trial a weight gain was 2-6.1 g. The mice were sacrificed by cervical dislocation at day 30. No translocation of lactobacilli or other bacteria of the microflora to blood or organs was detected at the autopsy.

TABLE 7

Total counts of lactobatsilli in faeces, ileum and colon

| Faecal samples | Sample | |
|---|---|---|
|  | Control group (cheese without *L. plantarum* Inducia DSM 21379 was administered) | Test group (cheese comprising *L. plantarum* Inducia DSM 21379 was administered) |
| Day 0 | 6.7 | 7.6 |
| Day 10 | 8.0 | 8.3 |
| Day 15 | 7.0 | 8.0 |
| ileum | 3.0-7.1/5.95* | 6.3-7.7/6.95* |
| colon | 4.4-7.3/6.65* | 6.9-7.8/7.45* |

*Student t-test p = 0.001

With seeding from ileum and colon from the mice administered with *Lactobacillus plantarum* Inducia DSM 21379 total counts of lactobacilli were found to be increased significantly both in ileum and colon.

Tissue samples from the liver, spleen, ileum and colon were fixed in formalin and embedded in paraffin. Microtome-cut tissue samples were stained with hematoxyline-eosine.

No morphological shifts were found in organs (liver and spleen), which proves the safety of *Lactobacillus plantarum* Inducia DSM 21379.

In the ileum quantity and shape of intestinal mucosa, count of goblet and Paneth cells was evaluated and formation of follicles and diffuse multiple deposits by lymphocytes.

In the colon attention was paid to the numerously goblet cells containing surface epithelium and to the characteristics of lymphatic tissue in connective tissue of mucosa.

TABLE 8

Patomorphological evaluation of mice organs after administration of *Lactobacillus plantarum* Inducia DSM 21379 comprising cheese.

| Mice group | Liver | Spleen | Ileum | Colon |
|---|---|---|---|---|
| *L. plantarum* Inducia DSM 21379 comprising cheese consumed animals | Hyperaemia 6/10* | ii | Lymph follicles 6/10* | Lymph follicles 8/10* |
| Control cheese consumed animals | Hyperaemia 3/10* | Hyperaemia 1/10 | Lymph follicles 3/10* | Lymph follicles 4/10* |

*$p < 0.05$

Administration of *Lactobacillus plantarum* Inducia DSM 21379 comprising cheese during 1 month enhanced liver hyperemia and raised significantly lymphatic follicles (immunocytes) of mice ileum and colon in comparison with control mice. These results refer to enhancement of the defence capability of intestinal mucosa and liver functions.

Example 4. Examination of Clinical Blood Indices of Healthy Volunteers Consumed *Lactobacillus plantarum* DSM 21379 Comprising Food and the Increase of *Lactobacillus plantarum* Percentage in the Intestinal Microflora The double-blind placebo-controlled (DBPC) cross-over exploratory trial (International registration number ISRCTN38739209) was conducted according to the guidelines of Declaration of Helsinki. The trial was approved by the Ethics Review Committee on Human Research of the University of Tartu, Estonia (approval number 158/10, 26.03.2007). All participants signed their written informed consent at the enrollment and were given the possibility to withdraw from the study any time.

The clinical trial with healthy volunteers evaluated the impact of putrescine, NO and antioxidative compounds producing *Lactobacillus plantarum* Inducia DSM 21379 comprising food consumption on (Estonian cheese) 1) safety for the consumer; 2) humoral and cell immunity parameters of blood; 3) effect on intestinal microflora; 4) and urine metabolites, to detect possible health-promoting effects.

The study group consisted of healthy volunteers, both male and female (M/F 4/8) aged 20-48 years. For exclusion criteria diabetes, glucose and glycohemoglobin HbA1c from blood sera were detected. The trial was randomized double-blind cross-over study. Trial started with 3-week consumption of test cheese. Volunteers consumed the test cheese for 3 weeks. After a 2-week washout period, volunteers were crossed over to another 3 weeks of control cheese administration.

*Lactobacillus planarum* Inducia DSM 21379 content in 30 old test cheeses was $6 \times 10^7$ cfu/g.

Before consumption the test cheese was incubated with *Lactobacillus plantarum* Inducia DSM 21379 for 30 days at 12° C. Regular Estonian cheese of Edam type without *Lactobacillus plantarum* Inducia DSM 21379 served as a control.

The trial was a randomized blinded cross-over placebo controlled trial. Trial started with 3-week consumption of test cheese, followed by 2 week washout period, after which the control cheese was consumed for 3 weeks. Dose 50 g/day.

Results

1) Safety

No discomfort, abdominal pain or other negative symptoms were reported by trial participants. After cheese trial with volunteers, the values of systemic inflammation markers (U-CRP, ultrasensitive CRP, and leucocytes) were not changed and were within the normal range.

The consumption of probiotic *Lactobacillus plantarum* Inducia DSM 21379 cheese did not cause changes in WBC counts (leucogram) (Table 9). No change was also detected in the values of essential allergy marker IgE in comparison with pre-trial period.

Consumption of *Lactobacillus plantarum* Inducia DSM 21379 comprising cheese had no negative impact on organisms' kidney and liver function nor affected according parameters (ASAT, ALAT albumine, blood sera creatinine).

Thus in healthy subjects the consumption of *Lactobacillus plantarum* DSM 21379 comprising cheese does not cause systemic inflammation, allergic sensibilisation or causes harm to essential organs.

2) Intestinal Microflora

Figure 2A:
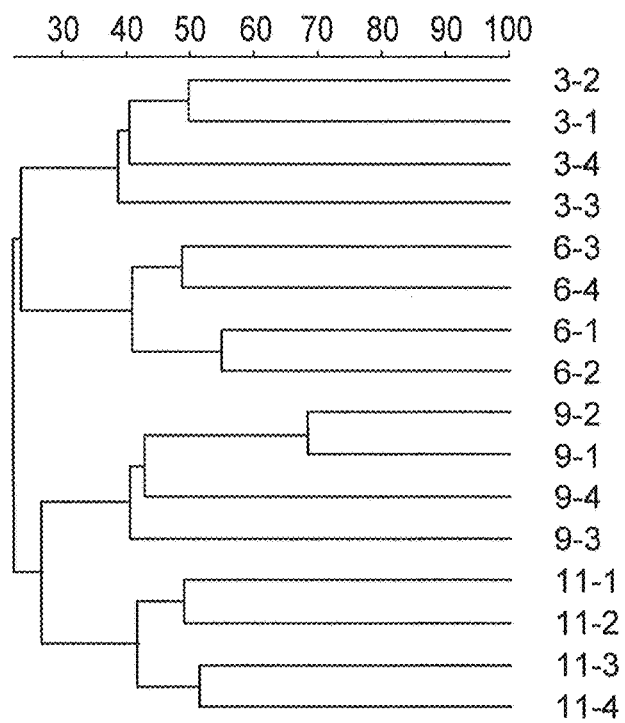
FIG. 2a, 2b, 2c. *Lactobacillus* species by Pearson UPMAG cluster analyses in *L. plantarum* Inducia DSM 21379 group.
Figure 2A:
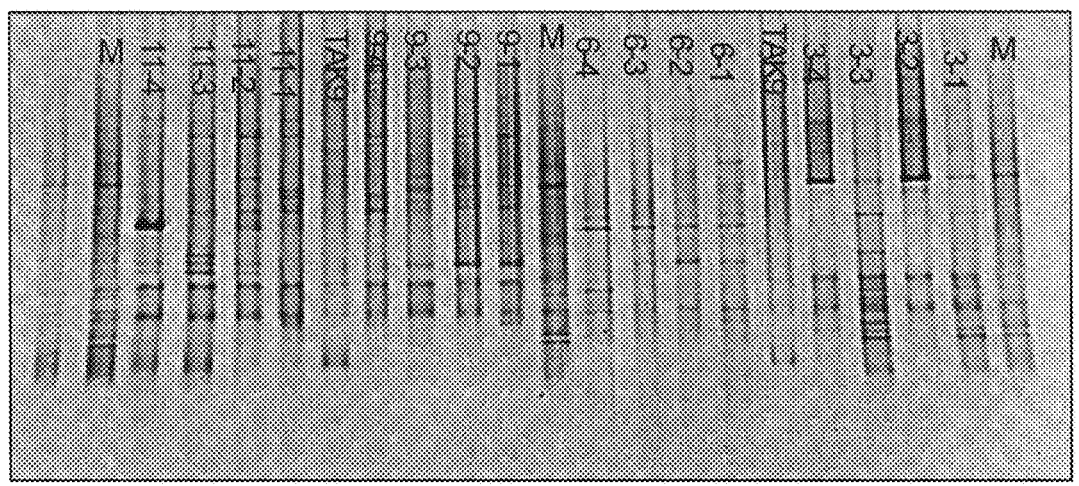
Figure 2B:
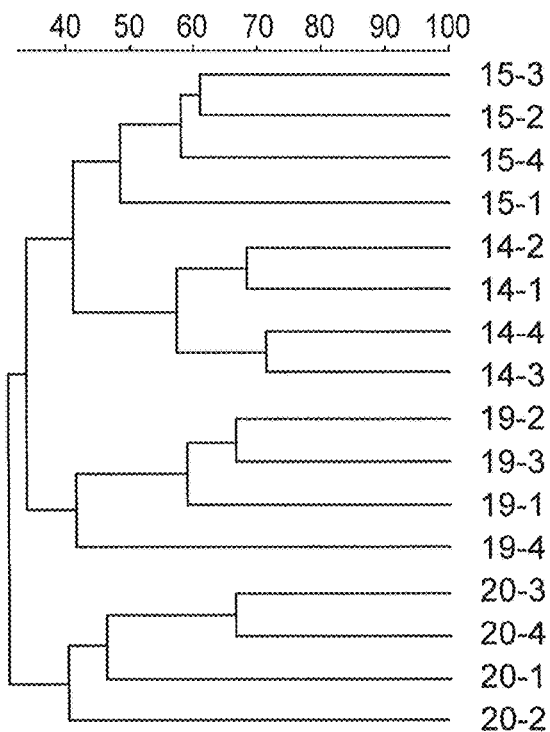
Figure 2B:
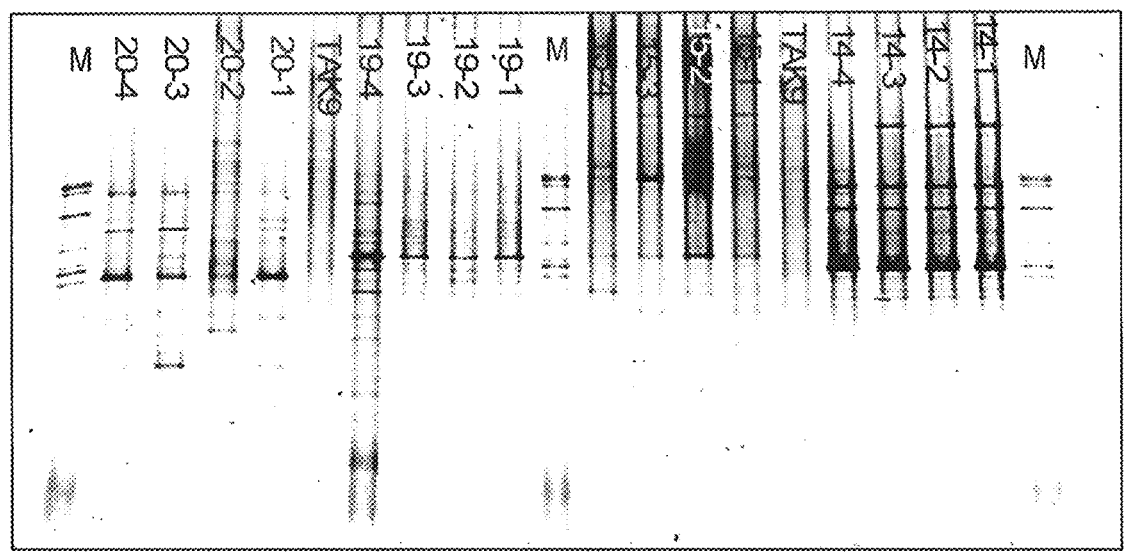
Figure 2C:
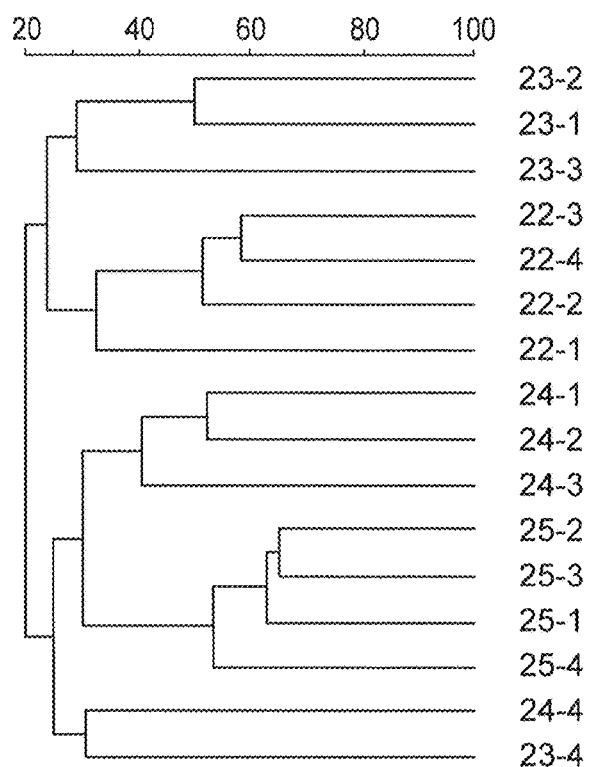
Figure 2C:
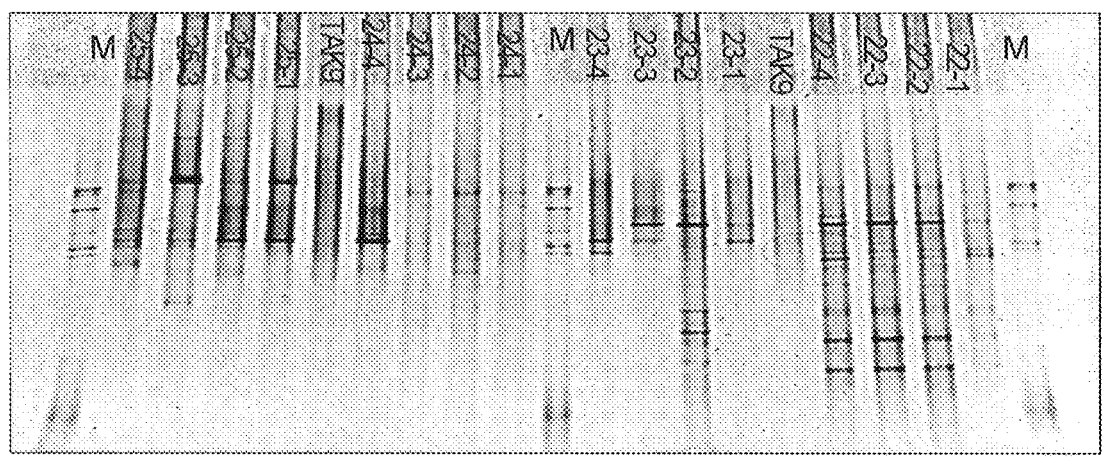

Method. Microbial DNA was isolated from cheese by QIAamp DNA Mini Kit (QIAGEN) and amplified with primers Uni-515-GC-rev (ATCGTATACCGCGGCTGCTG-GCA-GC), Lab-159-f (GGAAACAGA/GTGCTAATA-CCG) (Heilig H G, Zoetendal E G, Vaughan E E, Marteau P, Akkermans, A D L, de Vos W M, /et al./ Molecular diversity of /Lactobacillus/ssp. and other lactic acid bacteria in the human intestine as determined by specific amplification of 16S ribosomal DNA. /Appl Envir Microbiol/2002; 68: 114-123). Subsequently, the PCR product was separated by DGGE electrophoresis in 30-60% acrylamide containing gel with Dcode™ System technique. (Bio-Rad, Hercules, Calif.). Gels were analyzed by BioNumerics 2.5 (Applied Maths, Belgium) software according to Peasoni correlation (Fromin, N.; Hamelin, J.; Tarnawski, S.; Roesti, D.; Jourdain-Miserez, K.; Forestier, N.; Teyssier-Cuvelle, S.; Gillet, F.; Aragno, M.; Rossi, P. Statistical analysis of denaturing gel electrophoresis (IXGE) fingerprinting patterns Environmental Microbiology 2002; 4 (11), 634-643) (FIG. 2a, 2b, 2c).

Results

Consumption of *Lactobacillus plantarum* Inducia DSM 21379 comprising cheese changed lactobacilli pattern profile in feces in 5 persons of 12. These changes remained stable in 3 persons of 5 even 2 weeks after completing the trial.

Thus, consumption of *Lactobacillus plantarum* Inducia DSM 21379 comprising cheese affects the composition of human intestinal lactoflora.

3) Humoral and Cellular Parameters of Blood Sera

It appeared that *Lactobacillus plantarum* Inducia DSM 21379 comprising cheese induces the raise of cytokine IL-6, in volunteers, which indicates the stimulation of cellular immunity. This finding was confirmed by the increase of blood monocytes at the end of the trial ($p=0.015$), whereas indices of blood cells were within the normal range.

Positive correlation after completing the cheese consumption appeared between IL-6 and blood monocytes ($r=0.653$, $p=0.029$, $n=11$). The linear regression model confirmed the correlation ($R^2=0.405$, $R^2$ adj=0.338, =0.035)

Enhancement of parameters of cellular immunity is in accordance with results on animal model described above; where the administration of *Lactobacillus plantarum* Inducia DSM 21379 induced significantly Peyer's patches i.e. lymph follicles in the intestine. In these follicles interaction of the components of the immune system occurs. Proinflammatory cytokines incl. induction of IL-6 play important role in activation of TH1 type lymphocytes against bacteria through which macrophages i.e. blood monocytes are retroactive activated. Thereupon blood monocytes produce also IL-6.

The increase of the share of cellular immunity is explainable also by the suppression of humoral response e.g. somewhat decreased production of antibodies (IgA, IgG), which however remained within the normal range.

TABLE 9

Immunological parameters of blood after consumption of probiotic *Lactobacillus plantarum* Inducia DSM 21379 comprising cheese

| Immunity parameters | At the recruitment | End of the trial | P values | Normal range and units |
|---|---|---|---|---|
| Ultrasensitive CRP | 1.9 ± 1.6 | 3.3 ± 2.7 | 1.0 | <5 mg/L |
| Leukocyte counts ×10$^9$ | 6.3 ± 1.7 | 6.9 ± 1.6 | 0.116 | 4-10 × 10$^9$/L |
| Lymphocytes | 2.3 ± 0.5 | 2.2 ± 0.4 | 0.878 | 0.8-2.9 × 10$^9$/L |
| Monocytes | 0.55 ± 0.17 | 0.64 ± 0.15 | 0.032 | 0.15-0.75 × 10$^9$/L |
| Cytokine IL-6 | 2.7 ± 1.0 | 3.8 ± 1.7 | 0.020 | <3.4 ng/L |

TABLE 9-continued

Immunological parameters of blood after consumption of probiotic *Lactobacillus plantarum* Inducia DSM 21379 comprising cheese

| Immunity parameters | At the recruitment | End of the trial | P values | Normal range and units |
|---|---|---|---|---|
| IgA antibodies | 2.5 ± 0.9 | 2.3 ± 0.8 | 0.009 | 0.7-4.0 g/L |
| IgM antibodies | 1.3 ± 0.5 | 1.3 ± 0.5 | 0.776 | 0.4-2.3 g/L |
| IgG antibodies | 12.9 ± 3.2 | 12.4 ± 3.0 | 0.017 | 7.0-16 g/L |
| IgE antibodies | 19.6 ± 21.2 | 21.4 ± 25.9 | 0.232 | <85 kU/L |

4) The Urine Metabolites

For the evaluation of the content biogenic amines before the consumption of the probiotic and the efficiency of the stabilization period, the morning urine and gas chromatography method were used.

Method: urine samples were derivatized with propylchlorophormate for GC analyze by modified method of Uglandi (Ugland H G; Krough M, Rasmussen K E: Aqueous alkylchloroformate derivatization and solid-phase microextraction: determination of amphetamines in urine by capillary gas chromatography. *J Chromatography B Biomed Sci Appl* 1997; 701:29-38).

GC analysis were carried out by gas chromatograph HP 6890 Series GC System (Hewlett Packard, Avondale, Pa., USA), with capillar colonne HP-5 19091J-433 (30 m×0.25 mm; 0.25 m) The column temperature program 150° C. 1 min, 20° C./min 280° C. for 5 min; and detector (FID) 250° C. The biogenic amines concentration was calculated according to nmol/mol creatinine.

TABLE 10

Polyamines and biogenic amines content in the morning urine (nmol/mol creatinine) of probiotic cheese consumers

| | Probiotic cheese comprising *L. plantarum* Inducia DSM 21379 | | Control cheese (without *Lactobacillus plantarum* Inducia DSM 21379) | | |
|---|---|---|---|---|---|
| | BL1 mean ± stdev range (median) | PRO mean ± stdev range (median) | BL2 mean ± stdev range (median) | PL mean ± stdev range (median) | P values paired t-test BL1 vs PRO/ BL2 vs PL |
| Put | 0.064 ± 0.072 0-0.191 (0.030) | 0.082 ± 0.058 0-0.191 (0.077) | 0.043 ± 0.044 0-0.126 (0.033) | 0.044 ± 0.060 0-0.216 (0.031) | 0.432/0.432 |
| acPut | 0.606 ± 0.559 0.151-2.104 (0.435) | 1.087 ± 1.451 0.307-5.049 (0.447) | 0.796 ± 0.689 0.068-2.167 (0.600) | 0.635 ± 0.291 0.154-1.219 (0.594) | 0.021/0.850 |
| DAP | 0.079 ± 0.092 0-0.249 (0.055) | 0.059 ± 0.089 0-0.216 (0) | 0.056 ± 0.089 0-0.253 (0) | 0.117 ± 0.142 0-0.418 (0.055) | 0.411/0.195 |
| acSpd | 0.251 ± 0.227 0-0.813 (0.232) | 0.384 ± 0.198 0.043-0.686 (0.384) | 0.354 ± 0.210 0.085-0.668 (0.304) | 0.425 ± 0.260 0.065-0.831 (0.396) | 0.089/0.464 |
| Cad | 0.066 ± 0.123 0-0.364 (0) | 0.069 ± 0.162 0-0.569 (0) | 0.067 ± 0.093 0-0.293 (0.016) | 0.044 ± 0.085 0-0.228 (0) | 1.0/0.540 |
| His | 0.231 ± 0.226 0-0.595 (0.156) | 0.387 ± 0.524 0-1.401 (0.122) | 0.211 ± 0.364 0-1.229 (0) | 0.478 ± 0.684 0-2.093 (0.235) | 0.910/0.250 |
| Tyr | 0.153 ± 0.161 0-0.476 (0.102) | 0.101 ± 0.132 0-0.427 (0.050) | 0.093 ± 0.096 0-0.257 (0.093) | 0.212 ± 0.285 0-1.035 (0.179) | 0.167/0.149] |

Put—putrescine,
acPut—N-acetylputrescine,
DAP—1.3-diaminopropane,
acSpd—N 8-acetylspermidine,
Cad—cadaverine;
His—histamine,
Tyr—tyramine The content of polyamines (putrescine, acetylputrescine and acetylspermidine) in urine increased after consumption of *L. plantarum* Inducia DSM 21379 comprising probiotic cheese. A significant correlation (R=0.383 p<0.01, n=48) appeared between the contents of acetylputrescine and acetylspermidine in the urine of volunteers.

At the same time the content of all polyamines incl. putrescine, acetylspermidine and acetylspermine as well as biogenic amines remained within the normal range in the urine.

*Lactobacillus plantarum* strain inducia DSM 21379 is able to produce putrescine in vitro as well as in cheese. Consumption of probiotic *Lactobacillus plantarum* Inducia DSM 21379 cheese elevated the content of acetylputrescine in urine of trial participants.

Acetylputrescine represents a detoxified compound, elevated content of which proves putrescine production by *Lactobacillus plantarum* Inducia DSM 21379 in gastrointestinal tract of volunteers or absorption and metabolism of additional amounts of putrescine, consumed with cheese. On the other hand, this indicates the successful adaptational reaction of organism to deal with superfluous amounts of putrescine by excreting it with urine in acetylated form.

The immunostimulative effect of putrescine produced by *Lactobacillus plantarum* Inducia DSM 21379 was confirmed by the correlation between blood cytokine IL-6 and the quantity of macrophages (monocytes), which in this case could be considered activated macrophages. The finding mentioned together with $H_2O_2$ is essential for the organisms' defence against foreign cells (microbes, cancer cells).

Physiological doses of putrescine occurring in the gut due to *Lactobacillus plantarum* Inducia DSM 21379 could theoretically enhance the regeneration of the epithelium of intestinal mucosa and apoptosis of old cells, thus avoiding the hyperproliferation of epithelium. These mechanisms ensure the barrier function of intestinal mucosa and protects against penetration of allergens.

Consumption of *Lacrobacillus plantarum* Inducia DSM 21379 cheese regulates the amount and activity of blood monocytes through IL-6 which finding together with lymph follicles (increase of carriers of cellular immunity) demonstrated in experimental animals improves the barrier function of intestinal mucosa and supports organisms' immunological defence functions.

Example 5. Examination of the Clinical Blood Parameters of the Volunteers Consuming *Lactobacillus plantarum* Inducia DSM 21379 Containing Yoghurt The double-blind placebo-controlled (DBPC) cross-over exploratory trial (International registration number ISRCTN68198472) was conducted according to the guidelines of Declaration of Helsinki. The trial was approved by the Ethics Review Committee on Human Research of the University of Tartu, Estonia (approval number 178/T-13 19.01.2009). All participants signed their written informed consent at the enrollment and were given the possibility to withdraw from the study any time.

The objective of the clinical trial (randomised cross-over placebo controlled double-blind clinical trial, was to assess the safety and effect on the intestinal microflora of healthy volunteers of the *Lactobacillus plantarum* Inducia DSM 21379 containing yoghurt.

Subjects and Methods.

The participants were 27 voluntary healthy persons of both sexes (M/F 10/17, 29.2±9.3 yrs). For exclusion latent diabetes, glucose, and glycohemoglobione (HbA1c) were measured form blood serum. Test-yogurt contained *Lactobacillus plantarum* strain Inducia DSM 21379 ($5 \times 10^6$-$10^7$ efu/ml). Yoghurt without probiotic additive served as control. The trial started 3 week consumption of test-yoghurt, followed by a two-week washout period, after that the participants consumed the control yoghurt for 3 weeks. The daily dose was $10^8$-$5 \times 10^9$ cfu).

Serum Humoral and Cellular Immunity Parameters

It was found that yogurt containing *Lactobacillus plantarum* Inducia DSM 21379 induced chemoattractant protein (MCP, p=0.016) in the serum of volunteers, referring the stimulation of humoral part of the immune system. This finding was positively correlated with the increase of IL 10 (r=0.583; p=0.009).

The increase of the parameters of humnoral immunity was in accordance with the results obtained in the three weeks of administration of cheese comprising *Lactobacillus plantarum* DSM 21379 Inducia as described above.

TABLE 11

Content (pg/ml) of cytocines in the blood seerum of volunteers during the trial

| | Probiotic yoghurt | | Control yoghurt | | P valus BL1 vs PRO/ |
| --- | --- | --- | --- | --- | --- |
| | BL1 | PRO | BL2 | PL | BL2 vs PL |
| INFγ | 2.9 ± 4.3 | 3.8 ± 4.2 | 3.7 ± 3.6 | 1.9 ± 1.8 | 0.084/0.107 |
| TNFα | 4.6 ± 3.2 | 5.0 ± 2.6 | 4.0 ± 1.4 | 3.8 ± 1.2 | 0.225/0.376 |
| VEGF | 158.8 ± 15.8 | 157 ± 120.4 | 152.2 ± 106.8 | 163.0 ± 157.7 | 0.465/0.841 |
| MCP | 218.4 ± 98.1 | 251.3 ± 145.1 | 256.2 ± 142.2 | 230.8 ± 116.7 | 0.016/0.156 |
| EGF | 54.8 ± 57.6 | 53.4 ± 38.4 | 53.2 ± 56.5 | 52.0 ± 45.1 | 0.679/0.353 |

VEGF—vascular endothelial growth factor
MCP—monocyte chemoattractant protein
EGF—epidermal growth factor Thus, administration of *L. plantarum* Inducia containing yoghurt activated the monocyte chemoattractant protein, which demonstrates the increased immune activity.

After the administration of *Lactobacillus plantarum* Inducia containing yoghurt, the content of acetylated putrescine increased in the morning urine of patients.

The content of acetylated putrescine was correlated to (r=0.439 p=0.037) the increase of the amount of spermidine in the morning urine of patients.

These results are consistent with the results of the clinical trial of probiotic cheese. At the same time, the concentration of both polyamines incl. putrescine and acetylated putrescine as well as biogenic amines in the morning urine remained within normal limits.

TABLE 12

Content of polyamines and biogenic amines in the morning urine of the subjects consuming probiotic yoghurt (nmol/mol creatinine)

|  | Probiotic yoghurt | | Control yoghurt | | P values BL1 vs PRO/ |
| --- | --- | --- | --- | --- | --- |
|  | BL1 | PRO | BL2 | PL | BL2 vs PL |
| Put | 0.084 ± 0.170 | 0.032 ± 0.060 | 0.033 ± 0.039 | 0.029 ± 0.036 | 0.069/0.776 |
| acPut | 0.275 ± 0.231 | 1.015 ± 1.816 | 0.349 ± 0.240 | 0.538 ± 0.719 | 0.002/0.160 |
| DAP | 0 | 0.038 ± 0.109 | 0.005 ± 0.017 | 0.064 ± 0.200 | 0.181/0.059 |
| Spd | 0.168 ± 0.081 | 0.221 ± 0.147 | 0.188 ± 0.117 | 0.64 ± 0.269 | 0.218/0.377 |
| Cad | 0 | 0 | 0 ± 0.001 | 0.001 ± 0.005 | NA/1.0 |
| Tyr | 0 |  | 0 | 0 | NA |

Put—putrescine, acPut—N-acetylputrescine, DAP—1.3-diaminopropane, acSpd—N 8- acetylspermidine, Cad—cadaverine; Tyr—tyramine.

II. Use of *L. plantarum* Inducia DSM 21379 as Hypocholesterolemic Agent by Decreasing LDL-Cholesterol in Blood

Example 6. Bile Salt Hydrolase Activity of *L. plantarum* Inducia DSM 21379

Methods. Assessing the Bile Salt Hydrolase (BSH) activity *L. plantarum* Inducia DSM 21379 was performed according to Cuñé Castellana, 2009 (EP 2 485743 B1; AB Probiotics S.A.)

Three *Lactobacillus* spp strains were cultured overnight on MRS agar in microaerobic conditions at 37° C. After incubation, cultures were standardised to McFarland 3.0. The single-strain cultures were assayed for BSH activity. Cultures were impregnated around the sterilized paper disks on MRS agar plates supplemented with 4% (w/v) sodium salt of taurodeoxycholic acid (TDCA, Sigma, USA) and 0.37 g/l $CaCl_2$. Plates were anaerobically incubated at 37° C. for 72 h, and the diameter of the precipitation zones around the disks were measured. BSH activity was then calculated by subtracting the disc diameter (DD, mm) from the inhibition zone diameter (IZD, mm) and dividing this difference by two following the formula BSH activity=(IZD–DD)/2 (Table 13).

TABLE 13

Bile salt hydrolase (BSH) activity of *L. plantarum* Inducia DSM 21379

|  | BSH activity (mm) |
| --- | --- |
| *L. plantarum* Inducia DSM 21379 | 1.7 |
| *L. plantarum* BAA 793 | 1.5 |
| *L. gasseri* DSM 23882 | 0.75 |

BSH activity of *L. plantarum* Inducia DSM 21379 was higher than reference *L. plantarum* strain BAA793 and *L. gasseri* DSM 23882 (Table 13).

Example 8. LDL-Cholesterol Decreasing Ability of *L. plantarum* Inducia DSM 21379

The purpose of the human intervention trial ISRCTN79645828 "Effect of probiotic yoghurt on blood indices and intestinal microflora of healthy volunteers" was to assess the short term (3 weeks) LDL-cholesterol decreasing ability of *L. plantarum* Inducia DSM 21379 in volunteers blood when consumed with yoghurt comprising said strain.

Yoghurt preparation. The probiotic yoghurt was developed from adjusted and pasteurized (+92 . . . +95° C. 5 min) cow milk using *L. plantarum* Inducia DSM 21379 ($2 \times 10^{11}$ cfu/g) as an adjunct starter (inoculation dose 1 g/t). Shortly, the pasteurized milk was cooled to +35 . . . +43° C. before mixing with starter cultures and the probiotic strain. The milk was fermented until a pH 4.2 . . . 4.5 was reached and cooled to +23 . . . +27° C. The yoghurt was sweetened with 5% of sugar, packaged in plastic cups and cooled to +2 . . . +6° C. A yoghurt without probiotic adjunct served as a control.

Design of human volunteer trial. The double-blind placebo-controlled (DBPC) cross-over exploratory trial was conducted according to the guidelines of Declaration of Helsinki. The trial was approved by the Ethics Review Committee on Human Research of the University of Tartu, Estonia (approval number 190T-11, 2010). All participants signed their written informed consent at the enrollment and were given the possibility to withdraw from the study any time. The study was performed to investigate the effect of yoghurt comprising *L. plantarum* Inducia DSM 21379 on health biomarkers in healthy adults (n=49). Within one month prior to study participants were asked to continue their normal diet, and to avoid probiotic products (e.g. food supplements, yoghurts, cheese, kefir etc).

Two groups of participants started simultaneously with 3-week consumption of 150 g daily of test-yoghurt i.e. yoghurt comprising *L. plantarum* Inducia DSM 21379 ($4 \times 10^7$ cfu/g) or control yoghurt. The daily dose of the probiotic *L. plantarum* Inducia was $6 \times 10^9$ cfu. After a two-week washout period, the volunteers were crossed over to another three weeks period of consumption of the probiotic yoghurt or control yoghurt.

Clinical Investigations

The subjects were clinically investigated and blood plasma samples were collected after an overnight fast and abstinence from any medications, tobacco, alcohol and tea or coffee. Each participant was evaluated for anthropometrical indices. Body mass index (BMI) was calculated as the weight (kg) divided by squared height (m²). BMI was used to classify normal weight range (18.5-24.9 kg/m²), overweight (≥25.0 kg/m) and obesity (≥30.0 kg/m²) in healthy volunteers (WHO. The International Task Force. Obesity: Preventing and Managing the Global Epidemic. Report of a WHO Consultation on Obesity. Geneva, Switzerland. WHO/Nut/NCD/98. 1998; 1).

The samples of fasting blood were collected four times: at recruitment, after administration of either the *L. plantarum* Inducia DSM 21379 comprising product or control product, after wash-out period, and after the administration of the control or probiotic product at the end of the trial.

Haematological indices: plasma lipids: total cholesterol, LDL-cholesterol (LDL), HDL-cholesterol (HDL) and triglycerides were determined by standard laboratory methods using certified assays in the local clinical laboratory (United Laboratories of Tartu University Clinics, Estonia). Intervals for routine laboratory tests proposed by Nordic Reference Interval Project (NORIP, Rustard P., Felding P., Franszon L., Kairisto V., Lahti A., Martensson A., Hyltoft Petersen P., Simonsson P., Steensland H., Uldall A. (2004) The Nordic Reference Interval Project 2000: recommended reference intervals for 25 common biochemical properties. Scand J Clin Lab Invest 64: 271-284) were used as reference.

Change in oxidized LDL. (oxLDL, pmol/L) was measured by using the enzyme-linked immunosorbent assay (ELISA) kit (Mercodia, Sweden, Cat No 10-1143-01).

Statistical Analysis

Statistical analysis was performed by using R 2.10.1 (http://www.r-project.org Retrieved 25.03.2014) and GraphPad Prism version 4.00 for Windows (GraphPad Software, San Diego, Calif.). All data were expressed as mean and standard deviation (means±SD). Baseline and intervention data were compared by paired t-test or Wilcoxon rank sum test according to the distribution of data.

Differences were considered statistically significant if the value was p<0.05.

The two groups of healthy volunteers of the cross-over trial did not differ in their clinical data (Table 14).

TABLE 14

Baseline values of healthy volunteers

| | Group 1 n = 25 | Group 2 n = 24 | P value |
|---|---|---|---|
| Age | 35.8 ± 12.0<br>19.0-58.0<br>(34.0) | 38.0 ± 12.7<br>19.0-62.0<br>(36.5) | 0.617 |
| Sex F/M) § | 18/7 | 18/6 | 1.0 |
| HbA1c * | 5.5 ± 0.2 | 5.5 ± 0.3 | 0.976 |
| BMI | 23.8 ± 4.3<br>18.1-34.6<br>(22.7) | 25.2 ± 5.2<br>18.6-43.4<br>(25.3) | 0.297 |
| Waist//hip | 0.78 ± 0.06<br>0.68-0.97<br>(0.77) | 0.79 ± 0.07<br>0.68-0.94<br>(0.79) | 0.434 |
| Systolic blood pressure | 118.3 ± 10<br>101.0-144.5<br>(118.0) | 121.6 ± 15.5<br>98.5-158.0<br>(117.8) | 0.660 |
| Diastolic blood pressure | 77.5 ± 7.4<br>63.5-92.5<br>(76.7) | 78.6 ± 8.8<br>65.5-98.5<br>(79.3) | 0.719 |
| Cholesterol | 5.1 ± 1.1 | 5.2 ± 0.9 | 0.952 |
| LDL-cholesterol | 3.4 ± 1.0 | 3.4 ± 1.2 | 0.873 |
| HDL-cholesterol | 1.7 ± 0.4 | 1.7 ± 0.5 | 0.719 |
| Triglycerides | 1.2 ± 1.0 | 1.1 ± 0.3 | 0.298 |
| Glucose | 4.9 ± 0.5 | 4.9 ± 0.4 | 0.560 |

* glucohaemoglobin,
§ Fisher exact test

TABLE 15

Metabolic indices of blood sera during the trial

| | Probiotic yoghurt | | Control yoghurt | | P values<br>*BL1 vs PRO/<br>BL2 vs PL |
|---|---|---|---|---|---|
| | Baseline 1 | Probiotic period | Baseline 2 | Placebo period | (BL1 vs BL2,<br>PRO vs PL) |
| Cholesterol total | 5.2 ± 1.0<br>3.0-8.1<br>(5.1) | 5.1 ± 0.9<br>3.2-7.1<br>(5.0) | 5.1 ± 0.9<br>3.2-7.5<br>(4.9) | 5.1 ± 0.9<br>3.5-7.7<br>(5.0) | 0.081/1.0<br>(0.588, 0.172) |
| LDL-cholesterol total | 3.3 ± 1.0<br>1.3-6.2<br>(3.3) | 3.0 ± 0.9<br>1.2-5.0<br>(2.9) | 3.3 ± 1.1<br>1.1-6.1<br>(3.2) | 3.1 ± 1.0<br>0.9-5.6<br>(2.9) | <0.001/0.099<br>(0.358, 0.329) |
| HDL-cholesterol total | 1.7 ± 0.5<br>0.8-3.1<br>(1.8) | 1.7 ± 0.5<br>1.0-3.3<br>(1.7) | 1.7 ± 0.5<br>0.9-3.0<br>(1.8) | 1.7 ± 0.5<br>0.9-3.1<br>(1.7) | 0.569/0.402<br>(0.896, 0.788) |
| Triglycerides total | 1.1 ± 0.8<br>0.4-4.4<br>(0.9) | 1.1 ± 0.6<br>0.3-3.9<br>(0.9) | 1.1 ± 0.6<br>0.5-4.0<br>(1.0) | 1.1 ± 0.6<br>0.5-4.1<br>(1.0) | 0.694/0.456<br>(0.834, 0.412) |

*BL1: baseline 1; PRO: probiotic perioad, BL2: baseline 2; PL: placebo period

Change in oxidized LDL (oxLDL, pmol/L) value during the trial: at the start 52.7±16.2 49.0±15.3 vs at the end of the 3-week probiotic treatment, p=0.001)

The main changes after *L. plantarum* Inducia DSM 21379 consumption were revealed in the content of LDL-cholesterol particles. The LDL-cholesterol content was decreased after consumption of *L. plantarum* Inducia DSM 21379 comprising yoghurt (Table 15).

Thus, the consumption of *L. plantarum* Inducia DSM 21379 yoghurt during 3 weeks reduced the LDL-cholesterol level for 9.1% and the oxidized LDL level for 7% in blood.

III. Use of *L. plantarum* Inducia DSM 21379 as Antimicrobial Agent by Preventing Germination of Spores of *C. Difficile*

Example 9. Antagonistic Activity of *L. plantarum* Inducia DSM 21379 Against Vegetative Cells of *C. difficile* Reference Strains in Anaerobic Environment In Vitro The purpose of the study was to assess the antagonistic activity of *L. plantarum* Inducia DSM 21379 against *C. difficile* reference strains in anaerobic environment.

Methods. The tested strains were: *L. plantarum* Inducia DSM 21379 and *C. difficile* VPI 10463 (ATCC 43255), M 13042 hypervirulent strain.

Strains were seeded on solid media and incubated in an anaerobic environment. The suspension of bacteria in PBS was adjusted according to MacFarlandi standard (3 for $10^8$ cfu/ml). Suspension (0.2 ml) in the 200 ml BHI media was inoculated for reaching the concentration $10^5$ cfu/ml.

On different timescale the bacteriological seedings for growth were performed (0.1 ml) to MRS and LAB160 media. The plates were incubated in anaerobic and microaerobic conditions. The growth was checked after 2-5 days and the results were expressed as $\log_{10}$ CFU/ml.

TABLE 16

Inhibition of growth of *C. difficile* reference strains after co-cultivation with *L. plantarum* Inducia DSM 21379 in BHI media after 0, 24, and 48 h

| | Growth (log CFU/ml) | | |
|---|---|---|---|
| | 0 h | 24 h | 48 h |
| Growth of strains as single in BHI | | | |
| *L. plantarum* Inducia | 5.3 | 8.0 | 6.3 |
| *C. difficile* VPI 10463 reference strain | 5.8 | 4.6 | 7.5 |
| M 13042 clinical reference strain | 5.3 | 5.3 | 7.5 |
| Growth of *L. plantarum* Inducia and *C. difficile* strains after co-cultivation in BHI | | | |
| *L. plantarum* Inducia with *C. difficile* VPI | 5.8 | 8.8 | 7.3 |
| *L. plantarum* Inducia with M reference strain | 5.6 | 8.5 | 6.0 |
| *C. difficile* VPI10463 strain with *L. plantarum* Inducia | 5.5 | 0 | 0 |
| *C. difficile* M 13042 strain with *L. plantarum* Inducia | 5.3 | 0 | 0 |

Complete suppression of *C. difficile* vegetative cells by *L. plantarum* Inducia DSM 21379 was discovered after co-cultivation in BHI medium further seeded on selective MRS and CD LAB180 media after 48 h incubation *L. plantarum* Inducia DSM 21379 showed the highest values at 24 h in the BHI medium. After 48 h the growth yield of *L. plantarum* Inducia DSM 21379 was modestly suppressed equally in single culture (6.3 log cfu/g) or if combined with *C. difficile* strains (7.3 and 6.0 log cfu/g).

Example 4. Effect of Supernatant of *Lactobacillus plantarum* Inducia DSM 21379 on Vegetative Cells of *Clostridium difficile* Reference and Clinical Strains in Vitro The purpose of the following in vitro experiment was to determine the antimicrobial effect of *L. plantarum* Inducia DSM 21379 vegetative cells of on reference and clinical *C. difficile* strains. The distinction between the suppressive effect of natural (acidic) and neutralised supernatant (inhibitory substances e.g. peptides) of *L. plantarum* Inducia DSM 21379 helps to discriminate between two mechanisms—either impact of organic acids or presence of bacteriocins.

Material (strains) (Table 17)

*L. plantarum* Inducia DSM 21379

*Clostridium difficile* reference strains VPI 10463 and M 13042

*Clostridium difficile* clinical strains (11 strains)

Methods. Antimicrobial activity of *L. plantarum* Inducia DSM 21379 supernatant was determined against reference and clinical *C. difficile* strains by a microtitre plate (MTP) assay.

The *L. plantarum* Inducia DSM 21379 was maintained at −80° C. in microtubes on glass-beads and was activated trice in MRS broth with 0.15% agar, incubated under microaerobic conditions (10% $CO_2$) at 37° C. for 24 h. Overnight *L. plantarum* Inducia DSM 21379 culture was used to inoculate BHI broth 1% v/v and was incubated in microaerobic conditions for 24 h. For detection of antimicrobial activity of *L. plantarum* Inducia DSM 21379, the extracellular cell free supernatant (CFS) was collected by centrifugation from a 24 h old BHI broth cultures. The pH of cell free supernatant was measured and divided in half. The on half was left acidic and the other half was neutralized with 6N NaOH to pH 6.0, the both supernatants were filter sterilized.

*C. difficile* strains were maintained at −80° C. in microtubes on glass-beads and were activated trice on Fastidious Anaerobe Agar (FAA) with horse blood supplement for 24 h in anaerobic milieu (Anaerobic glove box, gases 90% N:5% $CO_2$:5% $H_2$). Overnight *C. difficile* cultures were used for the suspension with density according to MacFarland 3.0. For evaluating the antimicrobial activity of *L. plantarum* Inducia DSM 21379, 20 µl of *C. difficile* cell suspension was added to 180 µl: (1) BHI broth (as control), (2) cell free BHI supernatant, (3) cell free neutralized BHI supernatant, (4) diluted cell free supernatant (1:1 in sterile BHI broth) and (5) diluted neutralized cell free supernatant (1:1 in sterile BHI broth).

Growth of *C. difficile* (change in optical density values) was measured after 48 h at $OD_{620\,nm}$ using an MTP reader and the growth rates were calculated.

The suppressive activity of *L. plantarum* Inducia DSM 21379 was tested with Kruskal-Wallis test, where the growth density ($OD_{620\,nm}$) of *C. difficile* control was compared with the data of *C. difficile* growth density in natural and neutralised and in supernatants dilutions. The statistical analysis of data was performed using PAST Statistics Web provided program.

TABLE 17

Antimicrobial activity *L. plantarum* Inducia DSM 21379 supernatant neutral (acidic) and neutralised cell free supernatant and supernatant dilution against clinical and reference strains of *C. difficile* after 48 h of cultivation.

| *C. difficile* strains | The density of *C. difficile* in BHI (control) | The density of *C. difficile* in *L. plantarum* Inducia supernatant (natural or neutralized) | | The density of *C. difficile* in *L. plantarum* Inducia supernatant dilution 1:1 (supernatant: BHI) (natural or neutralized) | |
|---|---|---|---|---|---|
| | | natural | neutralized | natural | neutralized |
| CDE | 0.259 | 0.023 | 0.150 | 0.113 | 0.395 |
| CDP1 | 0.478 | 0.007 | 0.305 | −0.007 | 0.294 |
| CDP2 | 0.510 | 0.001 | 0.550 | 0.193 | 0.651 |
| CDP3 | 0.493 | 0.009 | 0.363 | 0.114 | 0.334 |
| CDP4 | 0.386 | 0.004 | 0.247 | 0.084 | 0.343 |
| CDP5 | 0.311 | 0.003 | 0.192 | 0.097 | 0.369 |
| CDP6 | 0.503 | 0.003 | 0.208 | 0.107 | 0.264 |
| CDP7 | 0.402 | 0.091 | 0.315 | 0.126 | 0.325 |
| CDP8 | 0.110 | 0.002 | 0.170 | 0.019 | 0.316 |
| CDP9 | 0.090 | 0.032 | 0.170 | 0.103 | 0.334 |
| CDP10 | 0.209 | 0.023 | 0.050 | 0.093 | 0.331 |
| VPI 10643 | 0.420 | 0.044 | 0.076 | 0.329 | 0.290 |
| M 13042 | 0.402 | 0.005 | 0.249 | 0.083 | 0.304 |
| Mean ± SD | $0.352 \pm 0.15^{a; b; c}$ | $0.019 \pm 0.03^{a; d; e; f}$ | $0.234 \pm 0.13^{b; d}$ | $0.112 \pm 0.08^{c; e}$ | $0.350 \pm 0.10^{f}$ |

$^{a}p < 0.0001$;
$^{b}p < 0.05$;
$^{c}p < 0.01$;
$^{d}p < 0.001$;
$^{e}p < 0.01$;
$^{f}p < 0.001$

Legend: vegetative cells of clinical strains: *C. difficile* CDE, CDP 1-9; reference strains: *C. difficile* VPI 10463 (ATCC 43255) and *C. difficile* M13042 (epidemic strain from Canada belonging to ribotype 027).

Thus, the strain *L. plantarum* Inducia DSM 21379 possess antimicrobial activity against *C. difficile* relying both on acid production in natural product (pH lowering) and in a smaller extent also on some antimicrobial protein-like substance still active after neutralisation of the supernatant (neutralized product) (Table 17).

Example 11. Testing of Growth and pH Values of *L. plantarum* Inducia DSM 21379 in the Media with Xylitol The purpose of the study was to find if xylitol influences the antagonistic activity of *L. plantarum* Inducia DSM 21379 against *C. difficile*.

Inducia ($10^5$ cfu/ml) was incubated in MRS media where glucose was substituted for 5% xylitol or used without sugar in microaerobic and anaerobic environment. The count of lactobacilli was registered as cfu/ml of media. We tested at 2, 6, 24, and 48 h if *L. plantarum* Inducia DSM 21379 uses xylitol for growth in vitro in microaerobic and anaerobic conditions.

At 24 h there was no difference in growth of *L. plantarum* Inducia DSM 21379 using media provided with xylitol or without it, at 24 h the growth in 5% of xylitole media was the best in microaerobic environment but a 2 log lower in anaerobic environment than that with glucose (Table 6).

TABLE 18

Counts of *L. plantarum* Inducia DSM 21379 (log cfu/ml) after growth in anaerobic and microaerobic conditions in modified MRS medium with 5% of xylitol or glucose

| Growth conditions | Sugar in the medium | The count of *L. plantarum* (log cfu/ml) after different time of incubation | | | | |
|---|---|---|---|---|---|---|
| | | 0 | 2 h | 6 h | 24 h | 48 h |
| Microaerobic | xylitol | 5.6 | 5.60 | 6.24 | 8.0 | 7.2 |
| | glucose | 5.41 | 5.48 | 6.94 | 8.8 | 9.0 |
| Anaerobic | xylitol | 5.6 | 5.70 | 6.00 | 7.4 | 7.15 |
| | glucose | 5.41 | 5.70 | 6.96 | 9.1 | 9.1 |

This experiment proved that *L. plantarum* Inducia DSM 21379 did not effectively metabolise xylitol in MRS media. The change of pH after growth of *L. plantarum* Inducia DSM 21379 in 5% xylitol containing modified MRS media was tested.

The lowest pH values by production of organic acids were seen in control media with glucose incubated in anaerobic environment. In xylitol containing media still a pH drop from pH 6.2 to pH 5.0 was seen both in microaerobic and anaerobic conditions, still substantially different from pH of control media with glucose from pH 7.5 to pH=3.2 (FIG. 3).

Use of xylitol in metabolism of *L. plantarum* Inducia DSM 21379

The purpose of the study was to measure the use of xylitol by *L. plantarum* Inducia DSM 21379 in microaerobic and anaerobic environments.

Methods: Double experiments were performed by cultivation of *L. plantarum* Inducia DSM 21379 in MRS medium with 5% xylitol in microaerobic and anaerobic environments for 2 to 120 h. Xylitol was detected with mass spectrometry QTRAP 3200 (Applied Biosystems, USA). The samples were centrifuged 3 min 10000 g, diluted 100 folds and 50 µl was mixed with 50 µl internal standard (5 mM D4-succinic acid in acetonitrile, 50 µl). 5 µl of dilutions were injected into mass spectrometry using 50% acetonitril/water eluent. The substrates were identified by multiple reaction monitoring (MRM) ionpairs 151/101 (xylitol) and 121/77 (internal standard). Concentration was calculated from a calibration curve made from solutions with known concentrations of commercial xylitol (Sigma-Aldrich, Germany).

In the repeated experiments Inducia used xylitol in very low amounts as the content of the sugar was sustained at Basal value±up to 0-0.6 mM of change (Table 19).

TABLE 19

Xylitol content (mM) after cultivation of *L. plantarum* Inducia DSM 21379 in 5% xylitol media microaerobically and anaerobically during 120 h

| Xylitol 1 (mM) | Repeated tests | 0 h | 2 h | 6 h | 24 h | 48 h | 120 h |
|---|---|---|---|---|---|---|---|
| 5% xylitol microaerobic | I | 3.1 | ND | 3.2 | 2.5 | 3.2 | ND |
|  | II | 3.4 | 3.4 | 3.3 | 3.2 | 3.3 | 3.3 |
| 5% xylitol anaerobic | I | 3.1 | ND | 2.8 | 3.2 | 2.5 | ND |
|  | II | 3.4 | 3.4 | 3.2 | 3.2 | 3.3 | 3.5 |

ND—not determined

Thus, we confirmed by mass spectrometry that *L. plantarum* Inducia metabolises xylitol in very low amounts.

Growth of *C. difficile* reference strains in environment containing xylitol and ampicillin The purpose of the study was to mimic in vitro the gut environment similar to elaborated *C. difficile* infection model in Syrian hamsters.

In vitro the impact of xylitol and ampicillin on growth of *L. plantarum* Inducia DSM 21379 and reference strains of *C. difficile* (VPI 10463 and the hypertoxic Ribotype 027 strain M 13042) in Brain Heart medium (BiII) was tested.

TABLE 20

Impact of different concentrations of xylitol (0.1-5%) and ampicillin (0.75 µl/ml) on 48 h growth of Clostridium difficile and *L. plantarum* Inducia DSM 21379 as single in anaerobic milieu and BHI medium

| Experimental modulators | *L. plantarum* Inducia log cfu/g | | *C. difficile* VPI log cfu/g | | *C. difficile* M strain log cfu/g | |
|---|---|---|---|---|---|---|
|  | 0 h | 48 h | 0 h | 48 h | 0 h | 48 h |
| BHI control | 5.9 | 9.8 | 5.3 | 7.2 | 4.9 | 7.1 |
| 0.1% xylitol | 5.3 | 8.0 | 4.7 | 6.4 | 5.0 | 6.9 |
| 1% xylitol | 5.0 | 8.0 | 5.5 | 7.3 | 4.8 | 6.7 |
| 2.5% xylitol | 5.5 | 8.3 | 5.0 | 6.7 | 5.0 | 6.0 |
| 5% xylitol | 5.5 | 7.8 | 5.0 | 7.1 | 5.0 | 6.7 |
| Ampicillin 0.75 µl/ml | 5.3 | 7.1 | 5.8 | 7.0 | 4.7 | 7.0 |

The *L. plantarum* Inducia DSM 21379 and the two reference strains of *C. difficile* increased the number of CFU nearly for 2 to 4 logarithms after 48 h of cultivation in the control media of BHI. No changes were seen after influencing *C. difficile* strains with xylitol and ampicillin (Table 20).

Growth of strain *L. plantarum* Inducia DSM 21379 was suppressed for ~2 logarithms both under 5% of xylitol and 0.75 µl/ml of ampicillin. Thus, in gut microenvironment with administered antibiotic ampicillin and up to 5% xylitole the survival of *L. plantarum* Inducia is granted.

Example 12. Growth of *L. plantarum* Inducia DSM 21379 and *C. difficile* Reference Strains by Co-Cultivation at Different Concentrations of Xylitol and Ampicillin The purpose of the study was to assess the growth of *L. plantarum* Inducia DSM 21379 and *C. difficile* reference strains by co-cultivation at different concentrations of xylitol and ampicillin.

The BHI media supplemented with 5% xylitol and 0.75 d/ml ampicillin were applied for co-cultivation of *L. plantarum* Inducia DSM 21379 and *C. difficile* reference strains in anaerobic environment (workstation Concept 400, UK) for 24 and 48 h.

The viability of *L. plantarum* Inducia DSM 21379, *C. difficile* VPI and M reference strains after cocultivation were tested as single in BHI media with ampicillin and xylitol 5% (1, 2a, 2b). After ten-fold serial dilutions for determining the count of *L. plantarum* Inducia in MRS broth was cultivated in $CO_2$ environment and for *C. difficile* on LAB160 media in anaerobic milieu.

TABLE 21

Inhibition of *C. difficile* reference strains with growth of *L. plantarum* Inducia DSM 21379 after co-cultivation in BHI with 5% xylitol and 0.75 µl/ml ampicillin after 0, 24, 48 h in anaerobic environment

| Strains/co-cultivation | | Growth (log, CFU/ml) | | |
|---|---|---|---|---|
|  |  | 0 h | 24 h | 48 h |
| 1. *L. plantarum* Inducia | | 5.7 | 8.5 | 7.3 |
| 2.a. *C. difficile* VPI | | 5.0 | 7.7 | 7.2 |
| 2.b. *C. difficile* M reference strain | | 5.0 | 7.3 | 7.3 |
| 3. *L. plantarum* Inducia | *C. difficile* VPI | 6.0 | 8.3 | 7.0 |
|  | M reference strain | 5.5 | 8.5 | 8.0 |
| 4. *C. difficile* VPI | *L. plantarum* | 5.0 | 0 | 0 |
| 5. M reference strain | Inducia | 5.0 | 5.0 | 2.0 |

During in vitro co-cultivation of *L. plantarum* Inducia DSM 21379 (3) and reference strains of *C. difficile* (4, 5) in the BHI medium with xylitol and ampicillin (mimicking the hamster model) the growth of vegetative cells of both *C. difficile* strains was suppressed. Full suppression was detectable for VPI strain and substantial reduction for 5 logarithms (from 5.0 to 2.0 log cfu/ml) was detected in the case of *C. difficile* strain M.

Thus, the in vitro experiments mimicking the gut environment of experimental hamster model after antibiotic treatment showed either full or high suppression of *C. difficile* growth with *L. plantarum* Inducia DSM 21379 alone (Table 5) or combined it with xylitol (Table 21).

Example 13. Animal Experiment

The purpose of the study was to assess the influence of *L. plantarum* Inducia DSM 21379 on *Clostridium difficile* reference strain VPI 10463 caused infection in the intestinal tract of *C. difficile* spores challenged hamsters.

Syrian hamsters (Mesocricetus auratus) provide a well-characterized model of Clostridium difficile infection. The colonic microbiota of hamsters treated with antibiotics is disrupted and if afterwards exposed to C. difficile spores, the animals develop C. difficile associated diarrhea (CDAD) in less than 48 h with 100% of mortality. We tested if mortality of C. difficile challenged hamsters can be decreased by administration of L. plantarum Inducia DSM 21379 according to our in vitro results.

First, we pre-feeded hamsters daily with L. plantarum Inducia DSM 21379 in the concentration of $10^{10}$ cfu/ml by gastric gavage with/without 1 ml 20% xylitol for 5 consecutive days before administration of ampicillin (30 mg/kg). The administration of L. plantarum Inducia DSM 21379 in the aforementioned concentration was continued during the whole experiment. On Day 7 the hamsters were infected with 10-30 spores of C. difficile VPI 104631. For next 5 days the health of hamsters was followed and in case of symptoms indicating CDAD: wet tail—the C. difficile A/B toxin test was performed (X/pect Remel test). The group of hamsters infected with C. difficile VPI strain served as a control group.

22). In this case the toxin tests were all negative in the survived hamsters (7/9), i.e. that the germination of spores C. difficile was suppressed. If xylitol alone was applied, the toxin tests of 4 out of 5 surviving animals were negative and only in one surviving animal the toxin test was positive.

Thus, the combination of xylitol with L. plantarum Inducia DSM 21379 works through suppression of germination of spores into vegetative cells of C. difficile able of toxin producing.

We tested if the growth of C. difficile was still present after the intervention with Inducia and xylitol and if the A and B toxins of C. difficile were found (Table 23). In survived hamsters prefeeded with combination of L. plantarum Inducia DSM 21379 and xylitol the C. difficile vegetative cells were not found 6/7 cases (only in one case the C. difficile growth was seen) in jejunum and ileum. Both the counts of anaerobes and L. plantarum Inducia substituting indigenous lactobacilli in jejunum and ileum were high showing the reconstruction and stabilisation of intestinal microbiota after

TABLE 22

Survival of C. difficile challenged hamsters (n = 15) pretreated with L. plantarum Inducia DSM 21379 and/or xylitol

| Test groups | Number of survived hamsters after challenge with C. difficile | | | | | Toxin test result/ number of animals in group | % of survival on Day 5 |
|---|---|---|---|---|---|---|---|
| | Day 1 | Day 2 | Day 3 | Day 4 | Day 5 | | |
| C. difficile VPI 104631 (n = 15) | 15 | 6 | 4 | 2 | 2 | 2 negative/15 | 2/15 13% |
| C. difficile VPI + Inducia (n = 5) | 5 | 2 | 2 | 1 | 0 | 0 negative/5 | 0/5 0% |
| C. difficile VPI + xylitol (n = 9) | 9 | 9 | 9 | 5 | 5 | 4 negative/9 | 5/9 56% |
| C. difficile VPI + xylitol + Inducia (n = 9) | 9 | 7 | 7 | 7 | 7 | 7 negative/9 | 7/9 78% |

Thus, the highest survival was found in case of combining L. plantarum Inducia DSM 21379 with xylitol solution pre-feeding prior to challenge with C. difficile spores (Table administration of ampicillin, challenge with C. difficile spores and usage of the treatment with L. plantarum Inducia DSM 21379 and xylitol.

TABLE 23

Total counts of anaerobes, lactobacilli, L. plantarum Inducia DSM 21379 and C. difficile in jejunum and ileum of survived hamster prefeeded with xylitol and L. plantarum Inducia DSM 21379

| Treatment groups | Hamster ID | Cd tox A/B test | jejunum (CFU log10/g) | | | | ileum (CFU log10/g) | | | |
|---|---|---|---|---|---|---|---|---|---|---|
| | | | AN | LB | Inducia | C.d | AN | LB | Inducia | C.d |
| C. difficile VPI + xylitol + Inducia (n = 7) | T2-1 | Neg | 6.48 | 0 | 4.00 | 0.00 | 7.48 | 0 | 6.70 | 0.00 |
| | T2-2 | Neg | 5.20 | 0 | 4.30 | 0.00 | 7.04 | 0 | 7.00 | 0.00 |
| | T2-3 | Neg | 7.48 | 0 | 4.30 | 0.00 | 7.30 | 0 | 6.70 | 0.00 |
| | T2-4 | Neg | 8.70 | 0 | 6.00 | 5.00 | 8.11 | 0 | 7.60 | 7.00 |
| | T2-5 | Neg | 4.48 | 0 | 0.00 | 0.00 | 7.30 | 0 | 6.00 | 6.00 |
| | T2-7 | Neg | 7.18 | 7.08 | 5.00 | 0.00 | 8.11 | 8.08 | 6.78 | 0.60 |
| | T2-8 | Neg | 8.34 | 6.70 | 6.00 | 0.00 | 8.43 | 7.65 | 6.00 | 0.00 |
| C. difficile VPI + | Xyl-1 | Neg | 5.30 | 3.00 | ND | 2.00 | 8.43 | 6.30 | ND | 0.00 |
| | Xyl-2 | Neg | 7.11 | 5.54 | ND | 0.00 | 8.30 | 5.00 | ND | 0.00 |
| | Xyl-3 | Pos | 7.60 | 4.00 | ND | 5.00 | 8.38 | 5.00 | ND | 7.60 |

TABLE 23-continued

Total counts of anaerobes, lactobacilli, *L. plantarum*
Inducia DSM 21379 and *C. difficile* in jejunum and ileum of survived hamster
prefeeded with xylitol and *L. plantarum* Inducia DSM 21379

| Treatment groups | Hamster ID | Cd tox A/B test | jejunum (CFU log10/g) | | | | ileum (CFU log10/g) | | | |
|---|---|---|---|---|---|---|---|---|---|---|
| | | | AN | LB | Inducia | C.d | AN | LB | Inducia | C.d |
| xylitol (n = 5) Pre-feeded | 24-1 | Neg | 7.35 | 7.6 | ND | 0 | 7.0 | 7.78 | ND | 0 |
| | 24-2 | Neg | 7.15 | 7.0 | ND | 0 | 7.8 | 7.78 | ND | 0 |

AN—anaerobes,
LB—lactobacilli;
C.d—*Clostridium difficile*

The survival rate of hamsters was 22% higher due to *L. plantarum* Inducia DSM 21379 (Table 22). This was proved also by absence of toxin from intestinal content of large intestine (Table 23).

The growth of *L. plantarum* Inducia was high in jejunum (range 0-6.0, median 4.0 CFU log 10/g and in ileum 6.0-7.6, median 6.7). *L. plantarum* Inducia DSM 21379 acted seemingly via its acid production through its SCFAs profile.

Morphological evaluation of the *C. difficile* infected hamsters

The typical CDAD infection was modelled in hamster model as in *C. difficile* infection the toxin damage of organs is the leading pathogenetic modulator.

In hamsters surviving the *C. difficile* infection and examined during autopsy no extensive damage of mucosa, no pseudomembranes and severe infiltration with polymorphonuclear cells was seen (FIG. 6 *a*).

Some hours before death the characteristic morphological finding of damaged with *C. difficile* infection hamsters was the inflammation with polymorphonuclear infiltration in mucosa and presence of pseudomembranes.

The severe enterocolitis developed the infiltration with red blood cells and polymorphonuclear leukocytes into gut mucosa, liver and spleen resulted in death of animals. In organs the hyperemia was present (FIG. 7 *a-f*).

SEQUENCE LISTING

```
<160> NUMBER OF SEQ ID NOS: 2

<210> SEQ ID NO 1
<211> LENGTH: 26
<212> TYPE: DNA
<213> ORGANISM: Unknown
<220> FEATURE:
<221> NAME/KEY: primer_bind
<222> LOCATION: (503425) (503404)
<223> OTHER INFORMATION: Designation Uni-515-GC-rev, location the
      sequence measured against the positive control Lactobacillus
      plantarum WCFS1

<400> SEQUENCE: 1
atcgtattac cgcggctgct ggcagc                                        26

<210> SEQ ID NO 2
<211> LENGTH: 21
<212> TYPE: DNA
<213> ORGANISM: Artificial sequence
<220> FEATURE:
<221> NAME/KEY: primer_bind
<222> LOCATION: (2181565) (2181551)
<223> OTHER INFORMATION: Designation Lab-159-f, location the sequence
      measured against the positive control Lactobacillus plantarum
      WCFS1

<400> SEQUENCE: 2
ggaaacagag tgctaatacc g                                             21
```

In our study the *C. difficile* VPI 10643 strain possessed both toxins A and B, and these were also present in liver and small intestine (FIGS. 4 and 5).

What is claimed is:
1. A method for decreasing the level of LDL-cholesterol in blood, and simultaneously for reducing the level of oxidized low density lipoprotein (ox-LDL) of blood of a subject by administering a daily dose of *Lactobacillus plantarum* Inducia DSM 21379 at $10^9$ CFU to a subject in need thereof during 3 weeks.

* * * * *